(12) United States Patent
Gabriel

(10) Patent No.: US 9,713,578 B2
(45) Date of Patent: Jul. 25, 2017

(54) FEEDING TUBE WITH INFLATABLE BALLOON COMPONENT

(71) Applicant: Sabry Gabriel, Lizella, GA (US)

(72) Inventor: Sabry Gabriel, Lizella, GA (US)

( * ) Notice: Subject to any disclaimer, the term of this patent is extended or adjusted under 35 U.S.C. 154(b) by 607 days.

(21) Appl. No.: 14/108,422

(22) Filed: Dec. 17, 2013

(65) Prior Publication Data

US 2014/0180252 A1 Jun. 26, 2014

Related U.S. Application Data

(60) Provisional application No. 61/739,836, filed on Dec. 20, 2012.

(51) Int. Cl.
| | |
|---|---|
| A61J 15/00 | (2006.01) |
| A61B 17/34 | (2006.01) |
| A61B 90/00 | (2016.01) |
| A61M 25/01 | (2006.01) |

(52) U.S. Cl.
CPC ....... *A61J 15/0026* (2013.01); *A61B 17/3415* (2013.01); *A61J 15/0003* (2013.01); *A61J 15/0007* (2013.01); *A61J 15/0049* (2013.01); *A61J 15/0073* (2013.01); *A61B 2090/0807* (2016.02); *A61B 2090/0811* (2016.02); *A61J 15/0092* (2013.01); *A61M 25/0127* (2013.01)

(58) Field of Classification Search
CPC ................ A61J 15/0026; A61J 15/0049; A61J 15/0003; A61J 15/0007; A61J 15/0073; A61J 15/0092; A61B 17/3415; A61B 2090/0807; A61B 2090/0811; A61M 25/0127

See application file for complete search history.

(56) References Cited

U.S. PATENT DOCUMENTS

| | | | |
|---|---|---|---|
| 4,244,362 A | 1/1981 | Anderson | |
| 5,318,530 A * | 6/1994 | Nelson, Jr. | A61J 15/00 604/103.1 |
| 5,431,640 A | 7/1995 | Gabriel | |
| 5,665,064 A * | 9/1997 | Bodicky | A61J 15/0069 600/156 |
| 2002/0160134 A1* | 10/2002 | Ogushi | A61M 16/0434 428/35.7 |
| 2005/0197667 A1* | 9/2005 | Chan | A61M 25/1025 606/194 |
| 2007/0049846 A1 | 3/2007 | Bown et al. | |
| 2009/0062772 A1* | 3/2009 | Wakeford | A61M 25/09041 604/516 |
| 2010/0030138 A1 | 2/2010 | Kantsevoy | |

* cited by examiner

Primary Examiner — Emily Schmidt
Assistant Examiner — Lauren M Peng
(74) Attorney, Agent, or Firm — Withers & Keys, LLC

(57) ABSTRACT

A feeding tube with an inflatable balloon component, a kit containing the feeding tubing, and a method for intubating a patient to deliver the feeding tube to a desired location for delivering nutrients and/or medication to the patient are described herein.

20 Claims, 17 Drawing Sheets

FEEDING TUBE WITH INFLATABLE BALLOON COMPONENT

CROSS-REFERENCE TO RELATED APPLICATIONS

This patent application claims the benefit of priority to U.S. Provisional Patent Application Ser. No. 61/739,836 filed on Dec. 20, 2012 and entitled "FEEDING TUBE WITH INFLATABLE BALLOON COMPONENT", the subject matter of which is hereby incorporated by reference in its entirety.

TECHNICAL FIELD

The present invention relates to medical catheters, particularly for use as feeding tubes.

BACKGROUND

Early, safe enteral nutrition provides several benefits to critically ill patients, including more rapid healing faster weaning from mechanical ventilation, fewer infections, and shorter hospital stays. A number of feeding tube devices have been developed over the years for the purpose of providing food and nutrients to a patient, such as into a patient's duodenum. For example, U.S. Pat. No. 5,431,640 issued to Gabriel, discloses a catheter guided by an external magnet so as to advance the catheter into the patient's duodenum. In addition, U.S. Pat. No. 6,126,647 issued to Posey et al. discloses a catheter guided by an external magnet, which contains a sensor that indicates whether the distal end of the catheter is being properly advanced into the patient's duodenum. The catheter contains a magnet that is permanently affixed in the distal portion of the catheter.

One current FDA approved device (i.e., the Gabriel Feeding Tube) uses an external magnet to direct duodenal intubation by a feeding tube with a magnet embedded in its tip. A light indicator at the proximal end of the feeding tube, connected to a magnetic field sensor at the distal end, provides confirmation to the operator that the magnet has been captured. In a study previously conducted at the Medical Center of Central Georgia, the enteral feeding tube with light indicator was reliably placed into the distal duodenum in an average of 17 minutes, with 87% success rate in the first attempt. This intubation technique did not require fluoroscopy, endoscopy or medications. Most of the 17 minutes were used to manipulate the tube from the first part of the duodenum to the 4th part of the duodenum. No attempts were made for deeper placements than 4th part of the duodenum as the anatomy is variable in different patients and even in the same patient at different times due to redundant omental attachment of the small intestine.

Risk associated with feeding directly into a patient's stomach is aspiration into the lungs. To minimize this risk, the tip of the feeding tube is advanced distally, ideally beyond the ligament of Treitz. Critically ill patients often have gastroparesis, but their small bowel function usually remains normal. Therefore, nasoenteral feeding in the distal duodenum can allow provision of daily caloric needs without the interruption required by gastric residuals. Unfortunately, placing enteral feeding tubes beyond the pyloric sphincter and even further into the duodenum is difficult. Many currently available tubes coil up in the gastric fundus.

Although known feeding tubes are designed to deliver food and nutrients to a patient, advancement of known catheters into the patient's duodenum continues to present a number of problems as discussed above.

There is a need in the art for improved feeding tube devices that more easily enter into and advance through a patient's duodenum.

SUMMARY

The present invention addresses the problems in the art by providing an improved feeding tube that more easily enters into and advances through a patient's duodenum. The disclosed feeding tube apparatus comprises an inflatable balloon component that can be inflated once the inflatable balloon component of the feeding tube apparatus passes through the pyloric sphincter of the patient. Once inflated, the inflatable balloon component of the feeding tube apparatus allows natural peristalsis of the patient to further advance the feeding tube apparatus into the patient's duodenum.

Accordingly, the present invention is directed to feeding tube apparatus comprising an inflatable balloon component. In one exemplary embodiment, the feeding tube apparatus of the present invention comprises a catheter suitable for use with a removable stylet, the catheter comprising a catheter proximal end, a catheter distal end opposite the catheter proximal end, a catheter channel extending along a length of the catheter from the catheter proximal end towards the catheter distal end, and an inflatable balloon component positioned along the catheter proximate the catheter distal end.

In another exemplary embodiment, the feeding tube apparatus of the present invention comprises (I) a catheter suitable for use with a removable stylet, the catheter comprising a catheter proximal end, a catheter distal end opposite the catheter proximal end, a catheter channel extending along a length of the catheter from the catheter proximal end towards the catheter distal end, and an inflatable balloon component positioned along the catheter proximate the catheter distal end; and (II) a removable stylet comprising a stylet proximal end and a stylet distal end opposite the stylet proximal end, the stylet distal end being sized so as to be insertable within (i) a catheter opening at the catheter proximal end, and (ii) the catheter channel.

The present invention is further directed to methods of using the disclosed feeding tube apparatus comprising an inflatable balloon component. In one exemplary embodiment, the method of using the disclosed feeding tube apparatus of the present invention comprises a method for intubating a patient so as to introduce one or more nutrients into the duodenum of the patient, wherein the method comprises: guiding a catheter of the feeding tube apparatus of the present invention through the patient's stomach until the inflatable balloon component of the catheter passes through the pyloric sphincter; and inflating the inflatable balloon component of the catheter so as to allow natural peristalsis of the patient to further advance the feeding tube apparatus comprising an inflated balloon component into the patient's duodenum.

The present invention is even further directed to kits that may be used in methods of providing nutrients to a patient. In one exemplary embodiment, the kit of the present invention comprises one of the disclosed feeding tube apparatus in combination with one or more additional kit components. Suitable additional kit components include, but are not limited to, an external magnet for advancing the disclosed feeding tube apparatus through a patient's stomach, a spring wire guide, a plunger, or any combination thereof.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION OF THE INVENTION

The present invention is directed to feeding tube apparatus comprising an inflatable balloon component. The present invention is further directed to methods of using feeding tube apparatus comprising an inflatable balloon component. The present invention is even further directed to kits that may be used in methods of providing nutrients to a patient.

The feeding tube apparatus of the present invention may comprise a number of components. A description of individual components and combinations of individual components is provided below.

I. Feeding Tube Apparatus Components

Figure 1A:
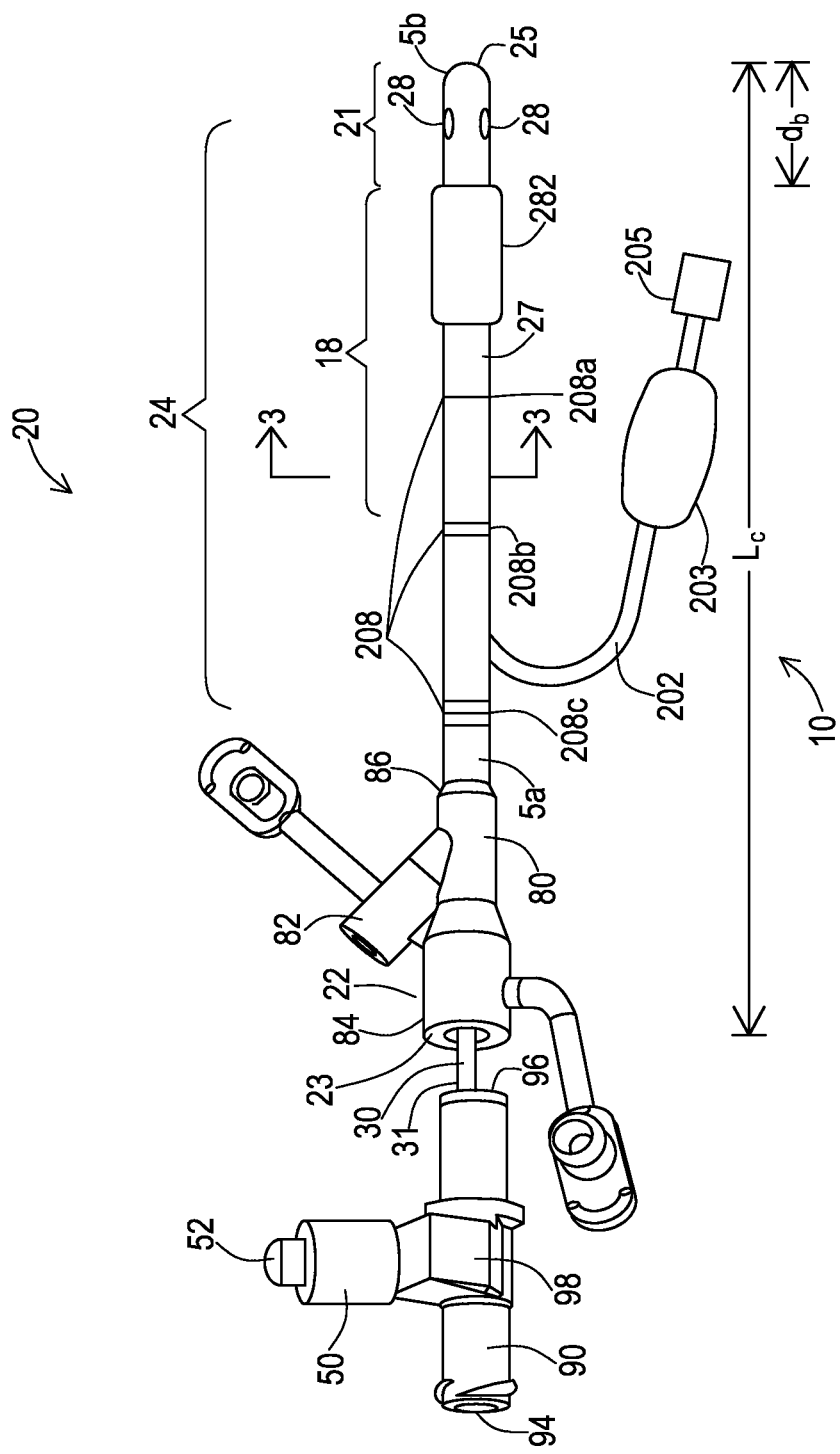
FIG. 1A depicts an exemplary feeding tube apparatus of the present invention with an exemplary inflatable balloon component in a non-inflated state.
Figure 1B:
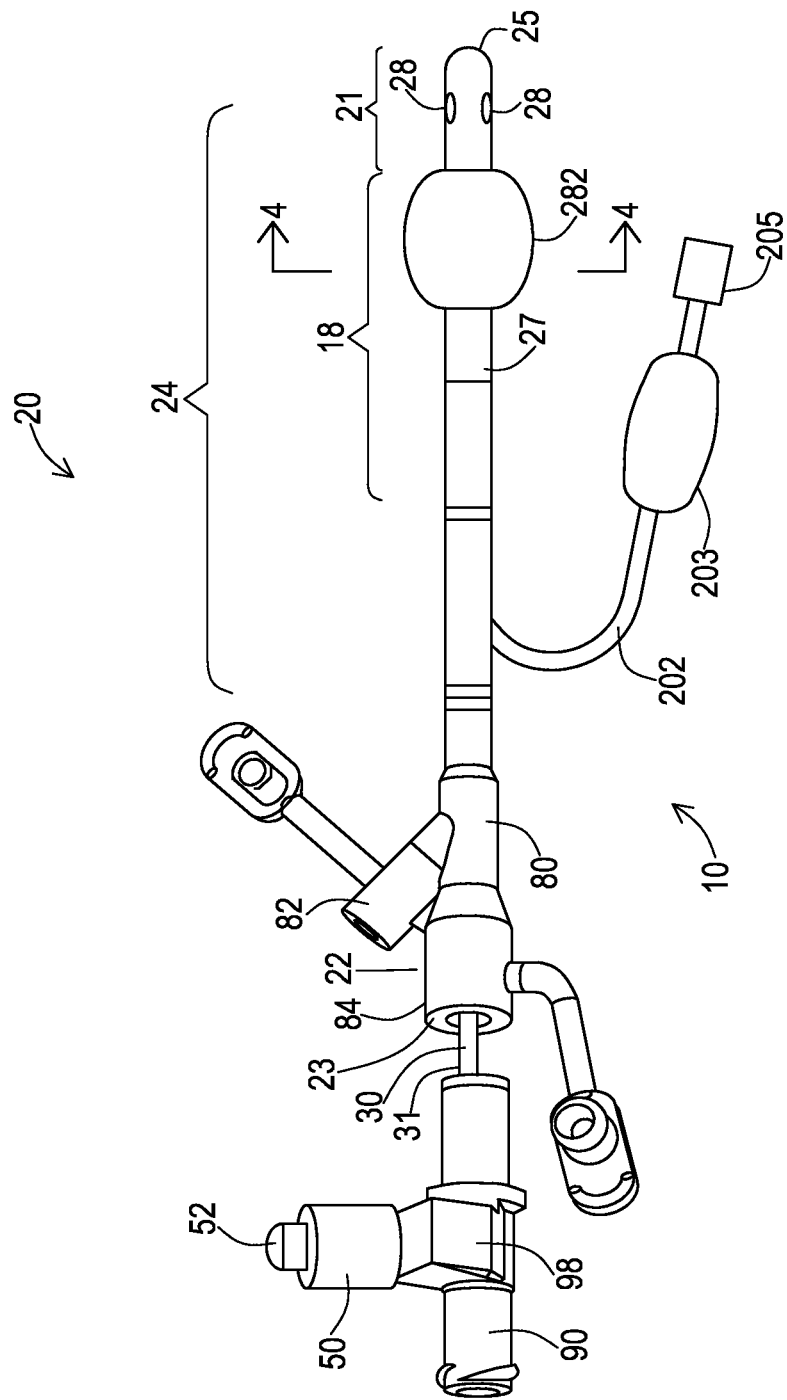
FIG. 1B depicts the exemplary feeding tube apparatus shown in FIG. 1A with the exemplary inflatable balloon component in an inflated state.

FIG. 1A depicts an exemplary feeding tube apparatus 10 of the present invention with an exemplary inflatable balloon component 282 in a non-inflated state. FIG. 1B depicts exemplary feeding tube apparatus 10 shown in FIG. 1A with exemplary inflatable balloon component 282 in an inflated state.

As shown in FIGS. 1A-1B, feeding tube apparatus of the present invention may comprise one or more of the following components.

A. Catheter

Feeding tube apparatus of the present invention, such as exemplary feeding tube apparatus 10 shown in FIGS. 1A-1B, comprise a catheter 20. Catheter 20 comprises a tube with a proximal end 22 and a distal end 24. Distal tip 25 of distal end 24 may be closed as shown in FIGS. 1A-1B, or may form an open lumen 266 as shown in FIGS. 2A-2B and 9-10C. Open lumen 266 allows for the delivery of food from distal tip 25 of catheter 20. Alternatively, distal tip 25 of catheter 20 is closed (as shown in FIG. 1A) and does not contain an open lumen. In this alternative embodiment, catheter 20 may contain one or more side holes 28 for food/nutrient delivery to a patient.

Figure 2A:
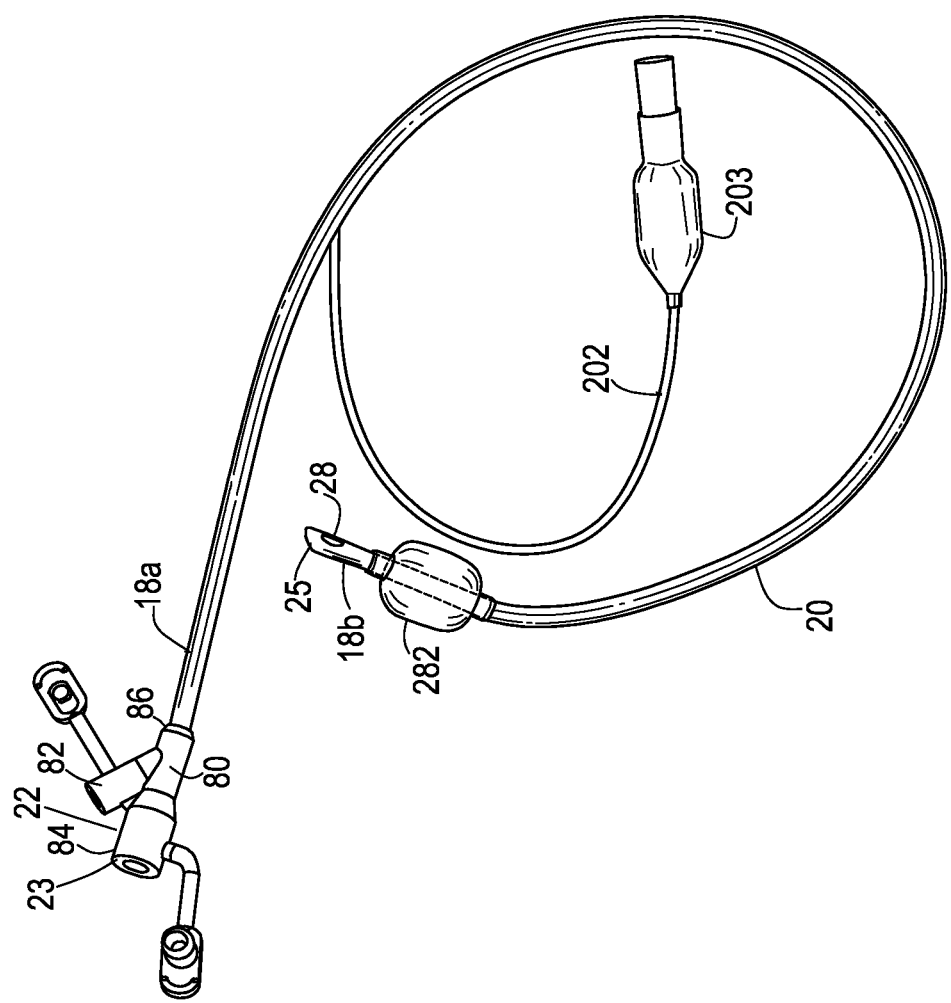
FIG. 2A depicts another exemplary feeding tube apparatus of the present invention with an exemplary inflatable balloon component in an inflated state.
Figure 2B:
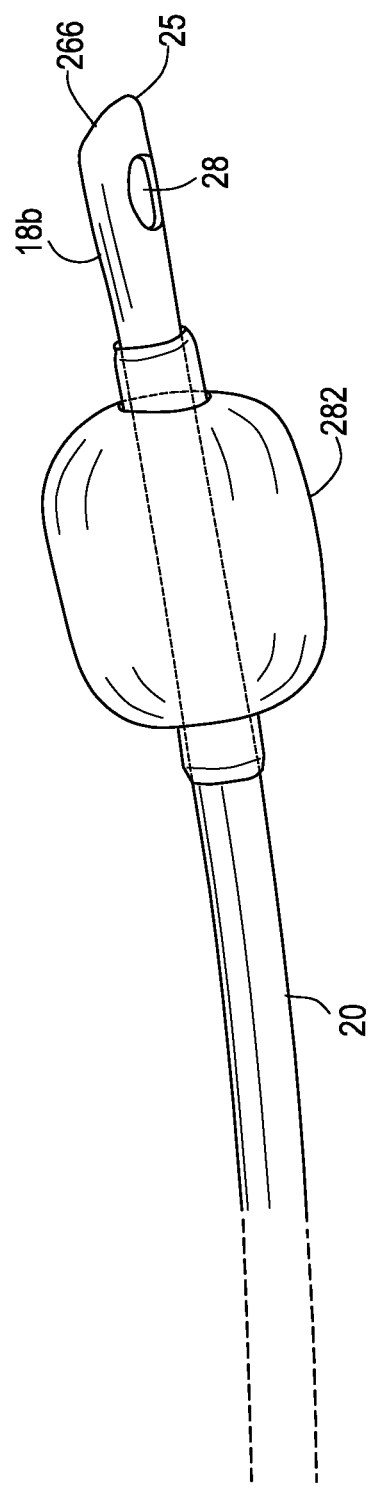
FIG. 2B depicts a close-up view of the distal end of the exemplary feeding tube apparatus shown in FIG. 2A.

As shown in FIGS. 2A-2B, even when distal tip 25 of distal end 24 forms an open lumen 266, catheter 20 may comprise one or more side holes 28 for food/nutrient delivery to a patient and/or aspiration of fluid from the stomach (e.g., sampling by aspiration using a syringe to test acidity or alkalinity using pH paper) through the one or more side holes 28. As shown in FIGS. 2A-2B, exemplary catheter 20 comprises an open lumen 266 at distal end 24, and a single side hole 28.

Distal tip 25 and the region 21 proximal to distal tip 25 may be formed of a softer material than the material that forms the rest of the catheter 20. This allows distal tip 25 and region 21 proximal to distal tip 25 to be atraumatic and allows magnetic material(s) 32 to have a more pronounced effect on maneuverability and guidance than they would if a stiffer material was used. Proximal end 22 of catheter 20 also forms an opening 23 into which removable stylet 30 is placed when inserted into catheter 20.

When distal end tip 25 comprises an open lumen 266, this allows for the use of a fiberscope, i.e. a flexible, small endoscope, which can be placed through open lumen 266 to verify the location of catheter 20. The use of a fiberscope can eliminate the need for X-rays to be taken to verify the location of the catheter 20.

Catheter 20 may be formed of any suitable tubing. Typically, suitable tubing materials have a flex modulus ranging from about 500 psi to about 50,000 psi, preferably from 700 psi to 3,000 psi, most preferably about 1,500 psi. In one exemplary embodiment, the tubing is dual durometer tubing, with at least two levels of flexibility; where the flex modulus for a first, softer portion is lower than the flex modulus for a second, more rigid portion. In one embodiment, proximal end 22 comprises a first, relatively soft material, and distal end 24 is more rigid than proximal end 22. In another exemplary embodiment, the tubing is relatively soft at the catheter's proximal end 22, at distal tip 25 and within region 21 proximate to distal tip 25, and is more stiff in the region 18 between proximal end 22 and region 21 proximate to distal tip 25. The soft material at proximal end 22, which will contact the patient's throat and nose, causes less irritation to the patient than a stiffer material. The soft portion of catheter 20 typically has a flex modulus ranging from about 500 psi to 30,000 psi, preferably ranging from about 750 psi to 3,000 psi. The stiffer material in region 18 between proximal end 22 and region 21 proximal to distal tip 25 allows catheter 20 to have greater pushability and maneuverability during insertion than if a softer material was included in region 18 of catheter 20. The stiffer portion of catheter 20 typically has a flex modulus ranging from about 1,500 psi to about 100,000 psi, preferably from about 10,000 psi to about 50,000 psi.

In one exemplary embodiment, catheter 20 is constructed in whole or in part of a medical grade radio-opaque material. Suitable medical grade radio-opaque materials include, but are not limited to, polyurethane, polyvinyl chloride (PVC) or silicon tubing. In some embodiments, the tubing comprises a polyurethane for strength. Preferably, the polyurethane material does not soften or change significantly at body temperature. Examples of suitable polyurethanes include, but are not limited to, those available under the trade designations ESTANE® (Lubrizol Advanced Materials, Inc.), PEBAX® (Arkema France Corp.), PELLETHANE® (Dow Chemical Co.), and CARBOTHANE® (Lubrizol Advanced Materials, Inc.).

Figure 3:
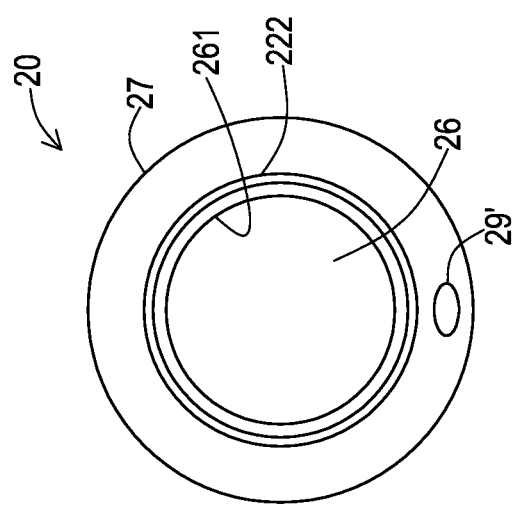
FIG. 3 depicts a cross-sectional view of the exemplary feeding tube apparatus shown in FIG. 1A along line 3-3 shown in FIG. 1A.
Figure 4:
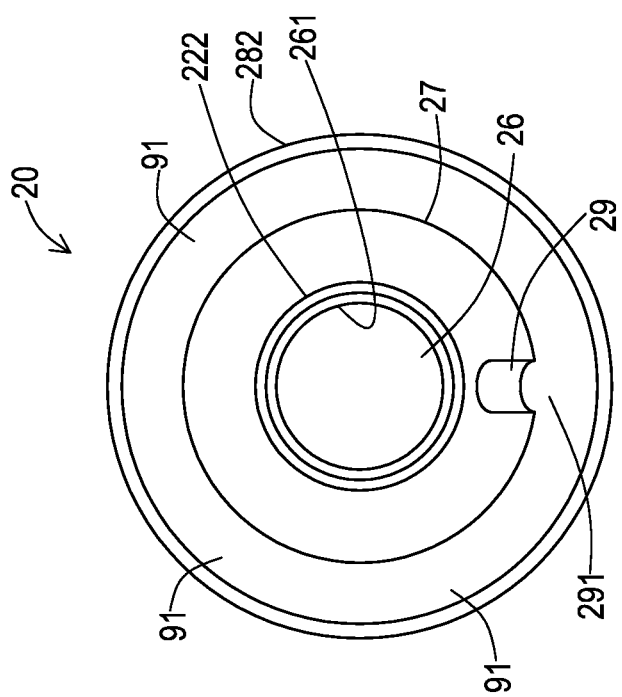
FIG. 4 depicts a cross-sectional view of the exemplary feeding tube apparatus shown in FIG. 1B along line 4-4 shown in FIG. 1B.
Figure 5:
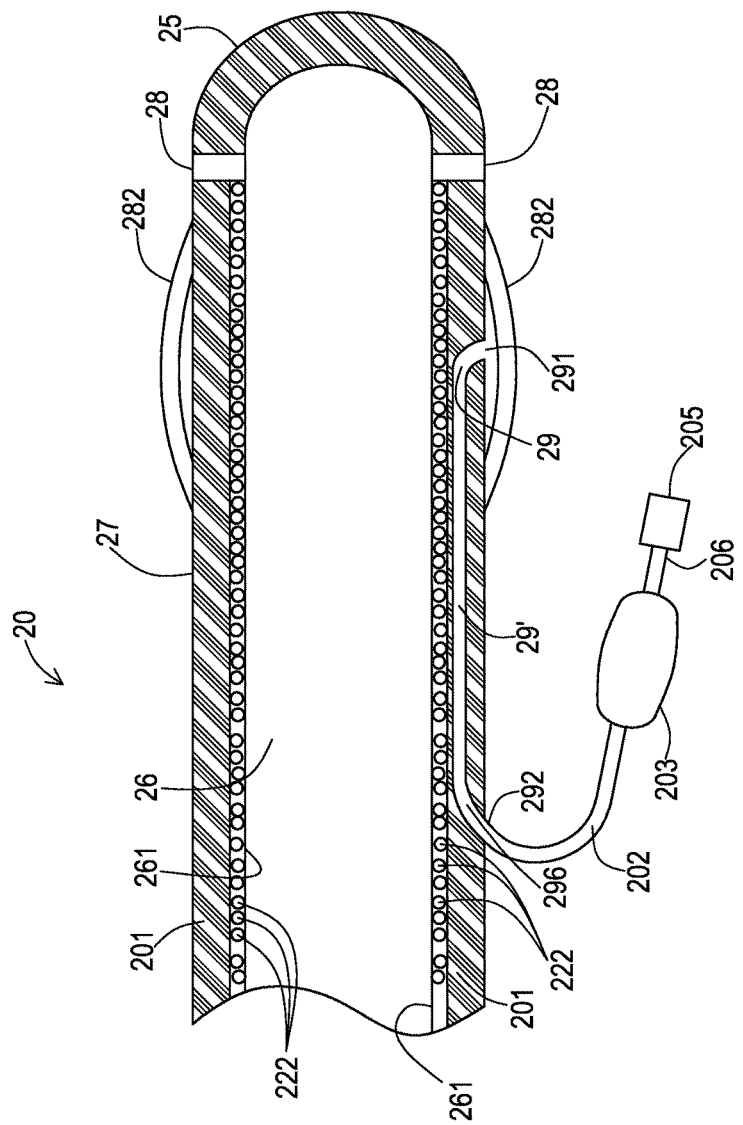
FIG. 5 depicts a cross-sectional view of a portion of the exemplary catheter within the exemplary feeding tube apparatus shown in FIG. 1A from point 5a to point 5b shown in FIG. 1A.

In some embodiments, the walls of the catheter may contain a reinforcing material 222 e.g., as shown in FIGS. 3-5. In these embodiments, the walls 201 of catheter 20 may contain, for example, an MRI compatible reinforcing material 222, such as a fiber, monofilament, or non-ferrous metal. This allows the catheter 20 to have a thin wall, while maintaining the desired inner diameter. Reinforcing material 222 also provides kinking and/or crush-resistance to catheter 20. Reinforcing material 222 also allows catheter 20 to be especially resilient to perforation, thereby facilitating the use of a plunger (not shown) to purge a clogged catheter 20 without the risk of perforating or damaging the feeding tube 10, even when the tube 10 is conforming to a tortuous path in the patient's body.

When present, reinforcing material 222 may be present as a coil reinforcing material 222 (e.g., a metal coil 222) as shown in FIGS. 3-5. Coil reinforcing material 222 may extend a complete length $L_c$ of catheter 20, or less than the complete length $L_c$. For example, in some embodiments, coil reinforcing material 222 extends the complete length $L_c$ of catheter 20 except for about one centimeter on either end of catheter 20. See, for example, FIG. 2A, wherein a metal coil reinforcing material (i.e., embedded within wall 201 or along an inner surface 261 of wall 201) extends from point 18a to point 18b along catheter 20. In other embodiments, coil reinforcing material 222 extends from about point 5a to one or more side holes 28 of catheter 20. In other embodiments, coil reinforcing material 222 extends from about point 5a to distal tip 25 of catheter 20.

In some embodiments, coil reinforcing material 222 is embedded within wall 201 of catheter 20 as shown in FIGS. 3-5. However, in other embodiments (not shown), coil reinforcing material 222 extends along inner surface 261 of wall 201 of catheter 20 so as to form an inner surface (i.e., that comes into contact with removable stylet 30). When coil reinforcing material 222 extends forms an inner surface of catheter 20, the contact surface of coil reinforcing material 222 (i.e., the surface that comes into contact with removable stylet 30) may further comprise a coating (not shown) that minimizes friction between catheter 20 and removable stylet 30.

Any standard diameter and length of tubing material may be used to form the catheter 20. Standard catheter sizes are referred to as "French" sizes, e.g. size F4 refers to a tube with a 0.053 inch outer diameter, F5 refers to a tube with a 0.066 inch outer diameter, F6 refers to a tube with a 0.079 inch outer diameter, F7 refers to a tube with a 0.092 inch outer diameter, F8 refers to a tube with a 0.104 inch outer diameter, F10 refers to a tube with a 0.131 inch outer diameter, F11 refers to a tube with a 0.143 inch outer diameter, and F12 refers to a tube with a 0.156 inch outer diameter. In one exemplary embodiment, the tubing is a single lumen 2603-80AE PELLETHANE® F11 or F12 tube. The F11 tube has an outer diameter of 0.143 inches and an inner diameter of 0.111 inches; and the F12 tube has an outer diameter of 0.156 inches and an inner diameter of 0.116 inches. However other size tubing is suitable as well. In place of single lumen tubing, double lumen tubing or alternative styles may be used. The inner diameter of the tubing (i.e. the diameter of the lumen) should be sufficiently large to allow the fluids and nutrients to pass through catheter 20 without clogging catheter 20. Typically, the inner diameter of the tubing (i.e. the diameter of the lumen) is sufficiently large to allow particles with a diameter of up to 0.110 inches to pass through the tubing.

The length of catheter 20 determines how deep into the gut the feeding tube 10 can be placed for the delivery of fluids and nutrients. Typical lengths for catheter 20 range from about 100 cm to about 150 cm. More typically, catheter 20 is at least 125 cm long. In one exemplary embodiment, catheter 20 is 127 cm long. This allows for nutrients to be delivered deep into the bowel and thereby prevent reflux. Catheters 20 that are at least 100 cm long prevent the patient from inadvertently removing the feeding tube 10 after placement in the stomach such as through standard movements.

In addition to openings 23 and 266 at proximal and distal ends 22 and 24 of catheter 20, catheter 20 may further comprise one or more side holes 28 along and within wall 201 of catheter 20. In some embodiments, side holes 28 are located as close to distal tip 25 as possible without compromising the strength of the tubing and interfering with magnetic material(s) 32 and reed switch assembly 60. In one embodiment, side holes 28 are located in region 18 between the proximal end 22 and inflatable balloon component 282. In another embodiment, side holes 28 are located within region 21 proximate to distal tip 25 of catheter 20.

Side holes 28 ensure that, even if feeding tube 10 is lodged against a wall in a patient's body, aspirating catheter 20 will not create a suction situation and potentially damage internal tissues or walls.

In one exemplary embodiment, catheter 20 comprises a single side hole 28 as shown in FIGS. 2A-2B. In another exemplary embodiment, catheter 20 comprises two side holes 28 as shown in FIGS. 1A-1B. Side holes 28 are typically oval or circular in shape and typically have dimensions ranging from about 0.060 inches to about 0.300 inches, more typically about 0.120 inches.

B. Inflatable Balloon Component

Feeding tube apparatus of the present invention, such as exemplary feeding tube apparatus 10 shown in FIGS. 1A-1B, further comprise an inflatable balloon component, such as inflatable balloon component 282. Inflatable balloon component 282 comprises an inflatable material that may be pliable or non-pliable. Suitable materials for forming inflatable balloon component 282 include, but are not limited to, polyvinyl chloride (PVC), silicon, latex, medical grade rubber, nitrile, and ChronoPrene™ material.

Inflatable balloon component 282 is positioned along an outer surface 27 of catheter 20, typically proximate distal end tip 25. Inflatable balloon component 282 may be attached to outer surface 27 of catheter 20 via any known method of attaching one material to another. Suitable ways to attach inflatable balloon component 282 to outer surface 27 of catheter 20 include, but are not limited to, adhesives, heat-bonding, ultrasonic welding, etc. Suitable adhesives include, but are not limited to, Permabond® 4C20 (an ethyl cyanoacrylate-containing composition), and Permabond® 4C10 (an ethyl cyanoacrylate-containing composition).

Figure 13:
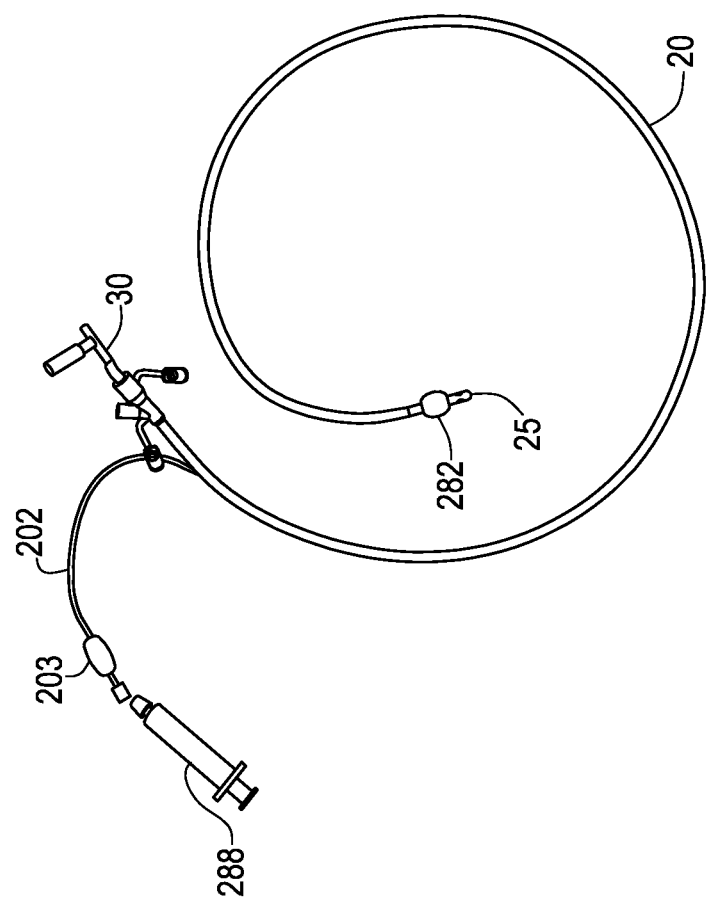
FIG. 13 provides a photograph of another exemplary feeding tube of the present invention.

Inflatable balloon component 282 may be inflated via at least one inflation tube 202 and an inflating device (e.g., a syringe 288 as shown in FIG. 13) as shown in FIG. 1A. Each inflation tube 202 may connect with an inflation channel 29' extending along a length $L_c$ of catheter 20 and within a sidewall 201 of catheter 20. Each inflating channel 29' comprising an inflating channel inlet opening 292 proximate catheter proximal end 22 and an inflating channel outlet opening 291 along an outer surface 27 of catheter 20 positioned underneath inflatable balloon component 282. FIG. 3 depicts a cross-sectional view of exemplary feeding tube apparatus shown in FIG. 1A along line 3-3 shown in FIG. 1A so as to illustrate an exemplary inflation channel 29'.

FIG. 4 depicts a cross-sectional view of exemplary feeding tube apparatus 10 shown in FIG. 1B along line 4-4 shown in FIG. 1B. As shown in FIG. 4, inflating channel outlet opening 291 is positioned along outer surface 27 of catheter 20 underneath inflatable balloon component 282.

FIG. 5 depicts a cross-sectional view of a portion of exemplary catheter 20 within exemplary feeding tube apparatus 10 shown in FIG. 1A from point 5a to point 5b shown in FIG. 1A. As shown in FIG. 5, inflating channel 29' comprising an inflating channel inlet opening 292 proximate catheter proximal end 22 and an inflating channel outlet opening 291 along an outer surface 27 of catheter 20 positioned underneath inflatable balloon component 282.

Each inflation tube 202 may be attached to catheter 20 via any known method of attaching one material to another. Suitable ways to attach inflatable balloon component 282 to outer surface 27 of catheter 20 include, but are not limited to, adhesives, heat-bonding, ultrasonic welding, etc. Suitable adhesives include, but are not limited to, Permabond® 4C20 (an ethyl cyanoacrylate), and Permabond® 4C10 (an ethyl cyanoacrylate). Further, although not shown in FIG. 5, a portion of inflation tube 202 may extend into and be attached to an inner surface 296 of inflating channel 29' proximate inflating channel inlet opening 292.

C. Removable Stylet

Feeding tube apparatus of the present invention, such as exemplary feeding tube apparatus 10 shown in FIGS. 1A-1B, may further comprise a removable stylet, such as removable stylet 30. Removable stylet 30 comprises a proximal end 31 and a distal end 34, with distal end 34 terminating in a distal tip 35. As shown in FIGS. 1A-1B, removable stylet 30 further comprises stylet hub 90, a stylet hub port 98 for attachment of a signal generator 50, and a signal indicator (e.g., LED light) 52, all of which are further described below.

Figure 6:
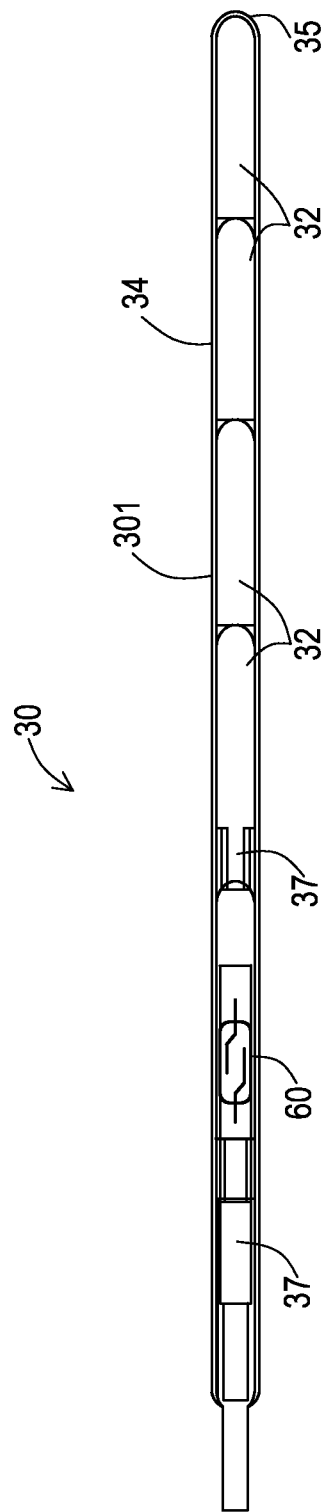
FIG. 6 depicts a cross-sectional view of a distal end portion of the exemplary stylet shown in the exemplary feeding tube apparatus of FIG. 1A.

FIG. 6 depicts a longitudinal section view of a distal end portion of exemplary stylet 30 shown in exemplary feeding tube apparatus 10 of FIGS. 1A-1B. As shown in FIG. 6, removable stylet 30 may comprise a number of additional components including, but not limited to, a reed switch assembly 60, a spacer 37, and one or more magnetic materials 32 therein. In this exemplary embodiment, a shrink wrap material 301 (i.e., a heat or non-heat shrink wrap material) is used to encompass and connect each of the above-mentioned components with one another. As discussed further below, a suitable shrink wrap material 301 may comprise, for example, a polyester material, and a polyolefin such as fluorinated polyethylene (FPE).

Figure 7:
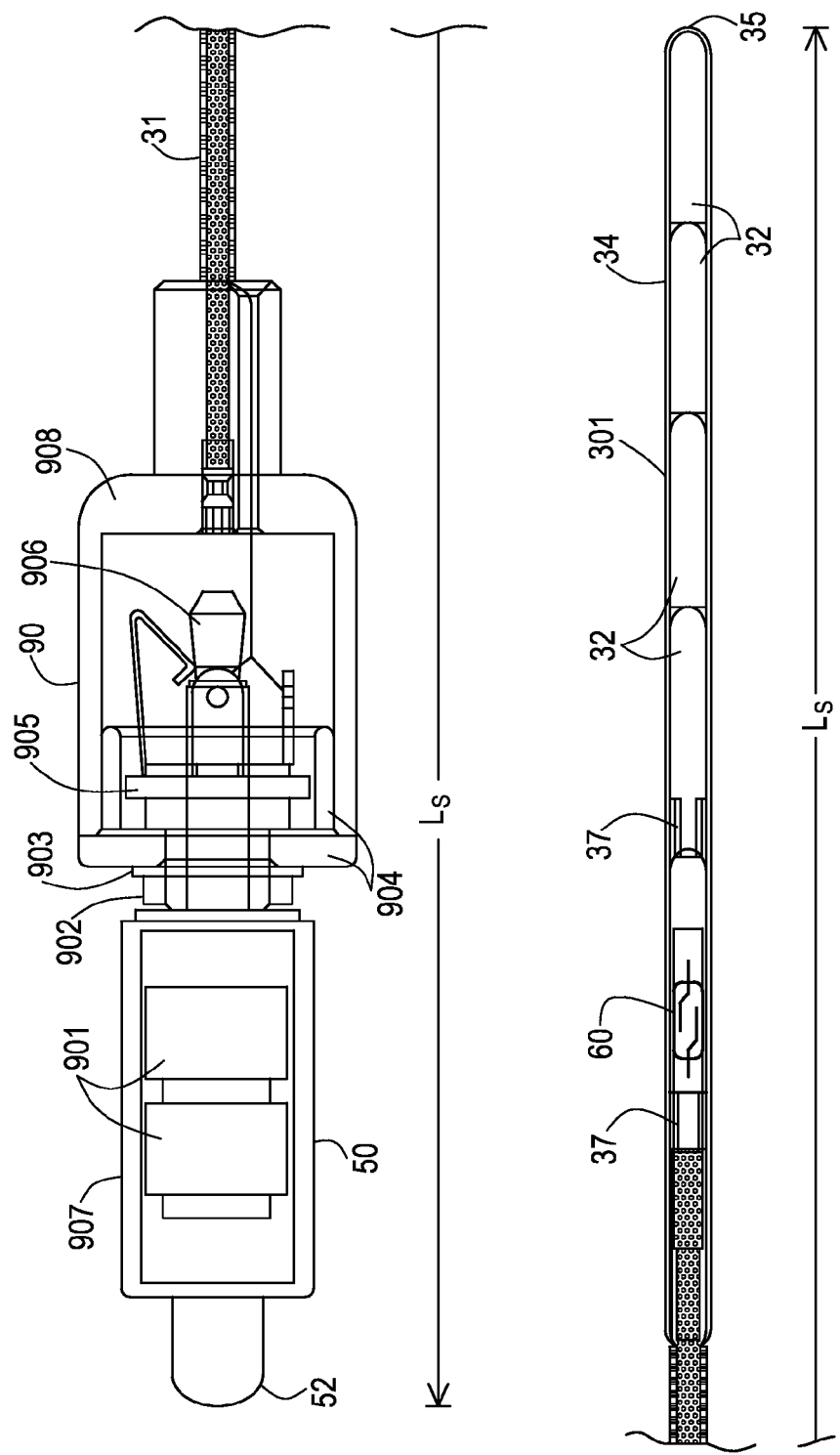
FIG. 7 depicts a cross-sectional view of another exemplary stylet suitable for use in the feeding tube apparatus of the present invention.
Figure 8:
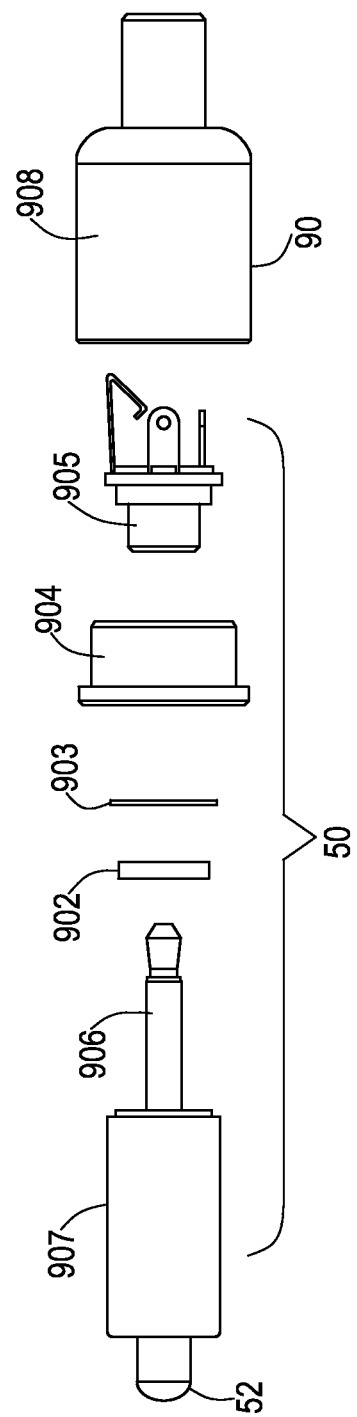
FIG. 8 depicts various components of the exemplary stylet shown in FIG. 7.

FIG. 7 depicts a cross-sectional view of another exemplary removable stylet 30 suitable for use in feeding tube apparatus 30 of the present invention. Like exemplary removable stylet 30 shown in FIGS. 1A-1B, exemplary removable stylet 30 shown in FIG. 7 may comprise one or more of the following components: stylet hub 90, signal generator 50, signal indicator (e.g., LED light) 52, reed switch assembly 60, one or more spacers 37, one or more magnetic materials 32 therein, and shrink wrap material 301, all of which are further described below. As further shown in FIG. 7, stylet hub 90/signal generator 50 comprise batteries 901 positioned within signal generator housing 907, locking nut 902, washer 903, LED hub end cap 904, RCA plug 905, RCA plug member 906 extending from signal generator housing 907, and LED hub 908. FIG. 8 depicts the various above-described components of exemplary removable stylet 30 shown in FIG. 7, separated from one another.

Figure 9:
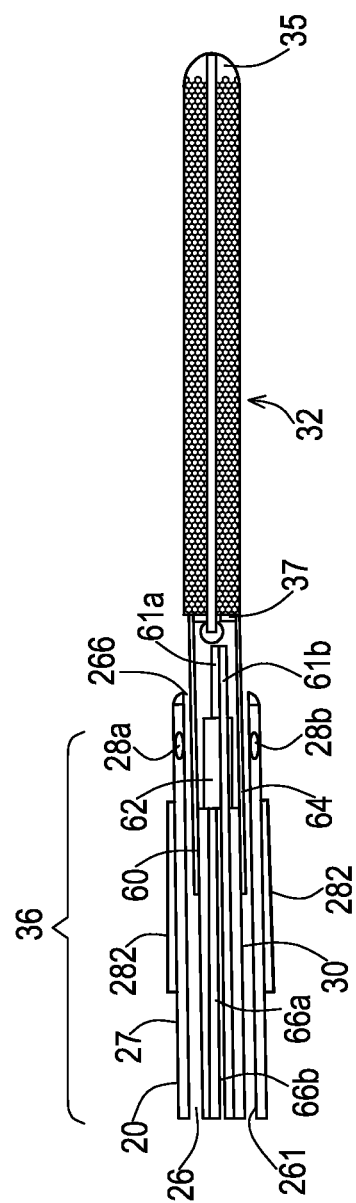
FIG. 9 depicts a longitudinal section view of the distal end of another exemplary feeding tube apparatus of the present invention.

FIG. 9 depicts a cross-sectional view of the distal end of another exemplary feeding tube apparatus 10 of the present invention. As shown in FIG. 9, catheter 20 comprises an open distal end tip 25 with lumen 266 therein, as well as side holes 28a and 28b. As further shown in FIG. 9, exemplary removable stylet 30 comprises magnet 32, reed switch assembly 60, and a flexible portion 36 (discussed further below).

Figure 10A:
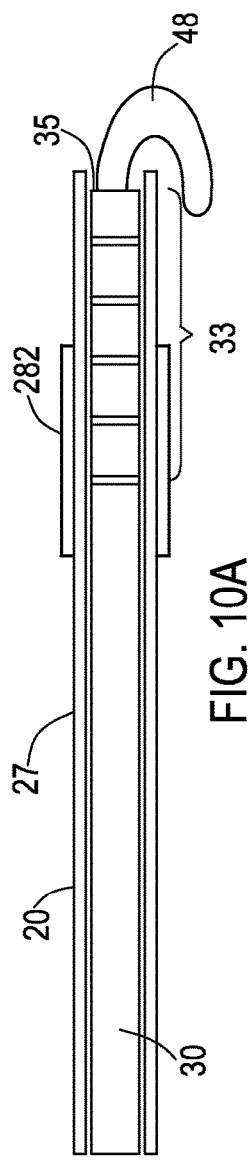
FIGS. 10A-10C depict cross-sectional views of three exemplary feeding tube apparatus of the present invention illustrating exemplary spring wire guide therein.
Figure 10B:
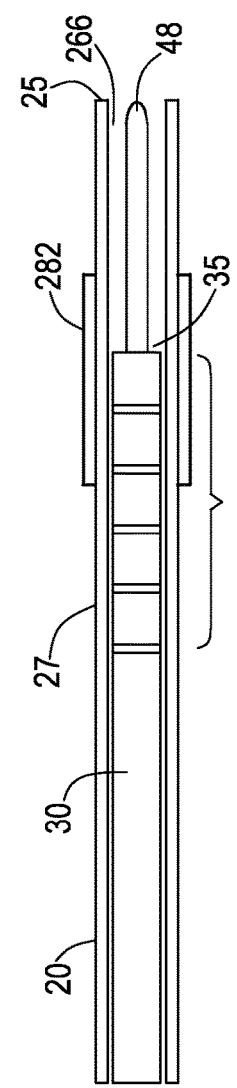
Figure 10C:
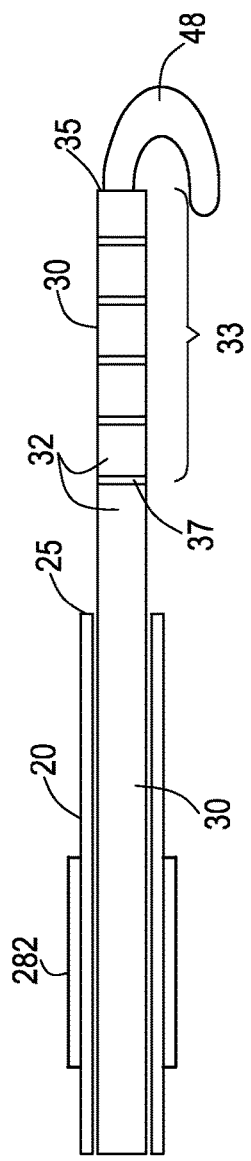

As shown in FIGS. 10A-10C, removable stylet 30 may comprise an additional element, such as a J-tip spring wire guide 48 or a pigtail-shaped spring wire guide 48, which is desirably attached to magnetic material 32 or magnet stack 32 and terminates at distal end 34 of stylet 32. When in use, the J-tip facilitates passage of stylet 30 through anatomical structures, particularly the duodenum, without catching on any anatomical pockets. Alternatively, instead of a J-tip, stylet 30 could contain a pigtail-shaped spring wire guide 48 which terminates at distal tip 35 of stylet 30, to achieve the same effect as a J-tipped spring wire guide 48. For example, in some embodiments, a pigtail-shaped spring wire guide 48 exhibits a pig-tail shape as it exits catheter distal end 25 making it less traumatic and unlikely to perforate the patient's intestine.

Removable stylet 30 is typically in the form of a tube and is typically formed of material that is more rigid than the catheter material. Typical flex modulus values for removable stylet 30 range from 125,000 and 350,000 psi, more typically from about 175,000 psi to about 250,000 psi, and even more typically about 200,000 psi. Suitable materials for forming removable stylet 30 include, but are not limited to, polycarbonate, polyether ether ketone (PEEK), nylon 6/6, stiff polyurethanes such as 75D PELLETHANE®, or another rigid material. Removable stylet 30 provides column strength to feeding tube apparatus 10 and facilitates guidance of catheter 20 during placement within the intestinal tract.

In some embodiments, removable stylet 30 is formed from a dual durometer material, i.e., a material with at least two levels of flexibility. In one exemplary embodiment, removable stylet 30 is formed from two different materials that are joined together, where one material is a stiffer material than the other material. Typical flex modulus values for a first, soft portion of removable stylet 30 range from about 25,000 psi to about 125,000 psi, more typically from 25,000 psi to 75,000 psi. Typical flex modulus values for a second, more rigid portion of removable stylet 30 range from about 125,000 to about 400,000 psi, more typically, about 250,000 psi. When two materials are used, desirably the stiffer material is used for the majority of the length of removable stylet 30, while the more flexible material is used for distal end 34 of removable stylet 30.

In another embodiment, removable stylet 30 is formed from a first material and contains a second material as a coating over the first material for a portion of the length of removable stylet 30, typically for the majority of the length of removable stylet 30, more typically only a portion of distal end 34 of removable stylet 30 is not covered by the second material. For example, in one embodiment, removable stylet 30 is formed from nylon, and the nylon is coated with a polyester shrink wrap (e.g., from Advanced Polymers, Inc.) along the majority of the length of removable stylet 30, with the exception of a portion of distal end 34, which contains only the nylon material and does not contain the shrink wrap coating. In this exemplary embodiment, distal end 34 is more flexible than the remainder of removable stylet 30. In one embodiment, the flexible portion 36 of removable stylet 30 (see, FIG. 9) is 3.0 inches in length. In other embodiments, the flexible portion 36 of removable stylet 30 may be from 1 inch to 6 inches in length. Removable stylet 30 is typically more rigid in a region that starts at proximal end 31 at stylet hub 90 and ends where the flexible portion begins. Typically, the flexible portion 36 typically begins immediately adjacent and proximate to reed switch assembly 60.

In one exemplary embodiment, removable stylet 30 is long enough to extend along the length of catheter 20, but not beyond distal tip 25 of catheter 20. In another exemplary embodiment, removable stylet 30 is long enough to extend along the length of catheter 20 and beyond open lumen 266 at distal tip 25 of catheter 20, which allows catheter 20 to track over a removable stylet 30 already in place in the desired location. Thus, removable stylet 30 can guide catheter 20 to its desired location, by passing catheter 20 over removable stylet 30 until it reaches the desired placement location.

Typical lengths for removable stylet 30 range from about 127 cm, which generally corresponds with the length of catheter 20, to a length greater than the length of catheter 20, such as about 175 cm, which allows for removable stylet 30 to extend beyond distal tip 25 of catheter 20. In one preferred embodiment, removable stylet 30 is about 127 cm long.

The outer diameter of removable stylet 30 is selected based on the inner diameter of catheter 20. The outer diameter of removable stylet 30 is less than the inner diameter of catheter 20 so that removable stylet 30 can easily slide into and out of catheter 20, as desired. By way of example, for catheters 20 formed using 11 FR or 12 FR tubing, removable stylet 30 may have an outer diameter from 0.030 to 0.107 inches.

In preferred embodiments, removable stylet 30 comprises magnetic material capable of interaction with an external magnet as discussed below. As used herein "magnetic material" refers to both magnets and magnetically attractive materials. Further, as used herein "magnet" refers to a material that both produces its own magnetic field and responds to magnetic fields. Magnets include permanent magnets, which remain magnetized, and impermanent magnets, which lose their memory of previous magnetizations. Magnets include but are not limited to the following materials: Neodymium (Rare Earth), Samarium Cobalt (Rare Earth), Ceramic (Ferrite), and Alnico (Aluminum Nickel Cobalt).

As used herein "magnetically attractive material" refers to materials that do not produce a magnetic field, but are attracted to a magnetic field or to each other when in the presence of a magnetic field, and include paramagnetic materials. Magnetically attractive materials include but are not limited to the following materials: iron, preferably iron coated with Teflon, polyimide, or parylene, or another suitable material to make it biocompatible, and steel.

As used herein "spacer" refers to a flexible material that neither produces its own magnetic field nor responds to magnetic fields. Materials that are useful for forming spacers include the above-described materials used to form catheter 20. Typical materials have a flex modulus ranging from about 500 psi to about 50,000 psi, preferably from 700 psi to 3,000 psi, most preferably about 1,500 psi. Examples of suitable materials include, but are not limited to, any flexible plastic, such as one formed from a soft polyurethane or silicon; examples include PEBAX®, PELLETHANE®, CARBOTHANE®, all in the 75 A to 55 D hardness range or thereabout.

In exemplary embodiments, distal end 34 of removable stylet 30 contains one or more magnetic materials 32, and preferably comprises a plurality of magnetic materials 32, optionally in combination with one or more spacers 37, referred to herein as a "magnet stack" 33. However, in select embodiments such as shown in FIG. 6, the dome, full radius-shaped distal end of the magnets offer flexibility of the magnet stack without use of flexible silicone spacers 37 therebetween.

Optionally, distal end 34 of removable stylet 30 contains a magnet stack 33 or a magnetic material 32 in the form of a continuous and flexible coil or wire strand. The length of magnetic material 32 or magnet stack 33 can be any suitable length for obtaining the necessary magnetic field between external magnet 40 and magnetic material(s) 32 or magnet stack 33 in removable stylet 30. Typical lengths for magnetic materials 32, when the magnetic material is a magnet, range from about 0.01 inches to about 0.5 inches, preferably from about 0.1 to about 0.4 inches, or from about 0.2 to about 0.600 inches. However, magnetically attractive materials may have the same dimensions as magnets. In one preferred embodiment, the length of each magnetic material 32 is about 0.400 inches.

Typical lengths for magnet stack 33 range from about 0.25 inches to about 2.0 inches. Typically, magnet stack 33 is about 1.6 inches long. Typical lengths for the magnetic material, when the magnetic material is a magnetically attractive material, range from about 0.25 inches to about 2.0 inches, more typically about 1.5 inches.

In one exemplary embodiment, the magnetic materials 32 are in the form of a stranded wire or a coiled assembly such as a helically wrapped wire (as shown in FIG. 9). This embodiment is particularly preferred for magnetically attractive materials. Preferably, the magnetically attractive material is iron, more preferably in the form of galvanized iron wire. The stranded wire and the coiled assembly construct should have suitable flexibility so that no spacers are needed. This embodiment allows for a continuous magnetically attractive material at the distal tip 35 of removable stylet 30.

One embodiment of device 10 which contains magnetic materials 32 in the form of a stranded wire or a coiled assembly is shown in FIG. 9. In this embodiment, removable stylet 30 contains reed switch assembly 60, which is located at distal end 34 of removable stylet 30 and is attached to spacer 37, which is attached to magnetic material 32 in the form of a stranded wire, or to a coiled assembly such as a helically wrapped wire.

The diameters for a magnetically attractive material in the form of coil or stranded wire are the same as the suitable diameters listed above for the magnetic materials in general.

Typical diameters range from about 0.050 inches to about 0.0125 inches, with a preferred diameter of about 0.080 inches in 12 French catheters. For example, the coil may be formed using a 0.020 inch diameter core with four (4) layers of 0.010 inch diameter iron wire. Thus the total diameter coil is about 0.1 inches. Alternatively, the magnetically attractive material may be in the form of a stranded wire. A 7×19 or similar stranded wire may be used to achieve a diameter of about 0.080 inches for 12 Fr catheters.

As shown in FIG. 9, removable stylet 30 may contain reed switch assembly 60 to ensure that indicator 52 properly indicates when the magnetic force between magnetic material(s) 32 or magnetic stack 33 in removable stylet 30 and external magnet 40 is sufficiently strong to move catheter 20) along the intestinal tract using external magnet 40. An example of a suitable reed switch assembly 60 is illustrated in FIG. 9 and further described in U.S. Pat. No. 6,126,647 to Posey et al., the subject matter of which is hereby incorporated by reference in its entirety. As shown in FIG. 9, reed switch assembly 60 contains reeds 61a and 61b sealed in a glass envelope 62, which is disposed within a metal housing 64. The leads 66a and 66b are soldered to external portions of reeds 61a and 61b, and metal housing 64 of reed switch assembly 60 is affixed to removable stylet 30 and thereby connects reed switch assembly 60, spacer 37, magnetic material(s) 32, and, optionally spring wire guide 48.

In some embodiments, magnetic material(s) 32, optionally in the form of a magnet stack 33, is coated with a biocompatible coating (not shown) that also provide a lubricious surface, such as parylene, to facilitate easy sliding of removable stylet 30 in and out of catheter 20. Alternatively, a shrink wrap tube 301, such as polyester heat-shrink material or FPE heat-shrink material, can be employed to encapsulate this assembly and thereby ensure that reed switch assembly 60, spacer 37, magnetic material(s) 32, and, optionally spring wire guide 48, do not separate from removable stylet 30. Shrink tubing 301 also provides a lubricious surface between inner surface 261 of catheter 20 and removable stylet 30 to facilitate insertion and removal of removable stylet 30 from catheter 20.

For an external magnet 40 having a magnetic flux field of about 300 Gauss at a distance of 4 inches from external magnet 40, reeds 61a and 61b in reed switch assembly 60 will contact each other, thereby actuating indicator 52, when external magnet 40 is within 3.5 to 5.0 inches of reed switch 60. In one embodiment, reeds 61a and 61b contact each other, thereby actuating indicator 52, when external magnet 40 is within about 4 inches of reed switch assembly 60. Indicator 52 produces a signal when it is actuated. The signal indicates that the magnetic force between feeding tube apparatus 10 and the external permanent magnet 40 is strong enough to use external magnet 40 to direct the feeding tube catheter 20 to the desired location.

Although removable stylet 30 is illustrated herein as containing a normally open reed switch assembly 60 disposed within metal housing 64, other reed switches, such as those that are normally closed, may be used. Other reed switches include, but are not limited to, single-pole, single-throw (SPST) normally-open reed switches, single-pole, single-throw (SPST) normally-closed reed switches, single-pole, double-throw (SPDT) normally-closed reed switches, and break-before-make reed switches. The stylet shown in FIG. 7 can also function as a spring wire (e.g., spring wire guide 48).

As discussed above, in addition to optionally containing magnetic material 32 or magnet stack 33, distal end 34 of removable stylet 30 may also contain a spring wire guide 48. The spring wire guide 48 may be a J-wire, a pigtail or a straight spring wire guide. An example of this embodiment is provided in FIGS. 10A-10C. Spring wire guide 48 facilitates guiding catheter 20 through the intestinal tract. In this embodiment, spring wire guide 48 is particularly useful at guiding catheter 20 after it passes through the pyloric valve, especially as it advances deep into the duodenum, while minimizing the risk of perforating the duodenal wall.

A pigtail can be formed at the distal tip 35 of removable stylet 30 to achieve the same effect as the J-wire. A pigtail is preferably formed from a flexible polyurethane, such as PELLETHANE®, PEBAX® or ESTANE®, such that it can easily be straightened when pulled into catheter 20, and once extended beyond catheter 20, can easily resume its pigtail shape to facilitate advancement of removable stylet 30 through the patient's body, especially in the duodenum while minimizing and/or eliminating the risk of perforating the duodenum.

Typically, catheter 20 is inserted into feeding tube hub 80, which contains one or more ports 82 to allow for aspiration or delivery of medications. Feeding tube hub 80 contains an opening at each end (i.e., proximal end 84 and distal end 86) and is hollow throughout the length of hub 80. Catheter 20 exits feeding tube hub 80 at the distal end 86 of feeding tube hub 80.

The proximal end 84 of feeding tube hub 80 attaches to the distal end 96 of stylet hub 90. Stylet hub 90 contains an opening at each end (i.e., proximal end 94 and distal end 96) and is hollow throughout the length of stylet hub 90. Removable stylet 30 exits stylet hub 90 at distal end 96 of stylet hub 90 and extends inside and along the length of catheter 20. Stylet hub 90 also contains a port 98 for connection to signal generator 50. Port 98 preferably contains a socket with which an LED plug can connect and thereby provide a visual signal when external magnet 40 is at an appropriate distance from magnetic material(s) 32. Signal generator 50 is electrically connected to reed switch assembly 60 via port 98.

Signal generator 50 includes a power source, such as one or more batteries 901 (shown in FIG. 7), which supply power to indicator 52 when reeds 61a and 61b close in response to a magnetic field supplied by external magnet 40 which is sufficiently strong to permit manipulation of distal end 24 of catheter 20 by movement of external magnet 40. Thus, when external magnet 40 is at the minimum distance required to supply a sufficiently strong magnetic field to allow external magnet 40 to manipulate the distal end 24 of catheter 20, reeds 61a and 61b in reed switch assembly 60 contact each other and thereby actuate signal generator 50.

Indicator 52 in signal generator 50 can produce any suitable signal that can be distinguished by a user, such as a light, a vibration, a sound, or a digital readout. In preferred embodiments, indicator 52 is a light, such as a light emitting diode (LED).

D. Optional Components

Feeding tube apparatus 10 of the present invention may further comprise a spring wire guide that is not attached to the stylet (not shown in figures). The spring wire guide may be a J-wire or a straight spring wire guide. In this embodiment, after removable stylet 30 is removed from catheter 20, the spring wire guide can be placed in catheter 20 until it protrudes from opening 266 at distal end 25 of catheter 20. Then, the spring wire guide can be used to facilitate guidance of catheter 20 as it advances through the intestinal tract. In other embodiments, stylet 30 has a stylet length $L_s$ of about 175 cm to achieve same function as the J wire.

Feeding tube apparatus 10 may also comprise a plunger (not shown in figures) that can clear debris that collects in catheter 20 to eliminate the need to remove catheter 20 and replace with another one. In this embodiment, after removable stylet 30 is removed from catheter 20, the plunger can be placed in the catheter 20 to remove any debris that is obstructing the delivery of nutrients and/or medicine to the patient, and/or preventing aspiration.

Optionally, distal end 34 of removable stylet 30 (or catheter 20) may further comprise a pH sensor probe (not shown), connected to a digital pH meter (not shown) at catheter proximal end 22. This allows one to measure the pH of the surrounding environment around catheter distal end 24 as feeding tube apparatus 10 is maneuvered through the patient to help determine when feeding tube apparatus 10 reaches the desired location for placement. In one exemplary embodiment, a pH sensor is mounted on the outer wall of catheter 20 for continuous or intermittent monitoring of pH.

II. Kits Comprising a Feeding Tube Apparatus

The present invention is also directed to kits that may be used in methods of providing nutrients to a patient. The kits of the present invention comprise one or more of the feeding tube apparatus described above. The kits may further comprise one or more external magnets 40.

Figure 11A:
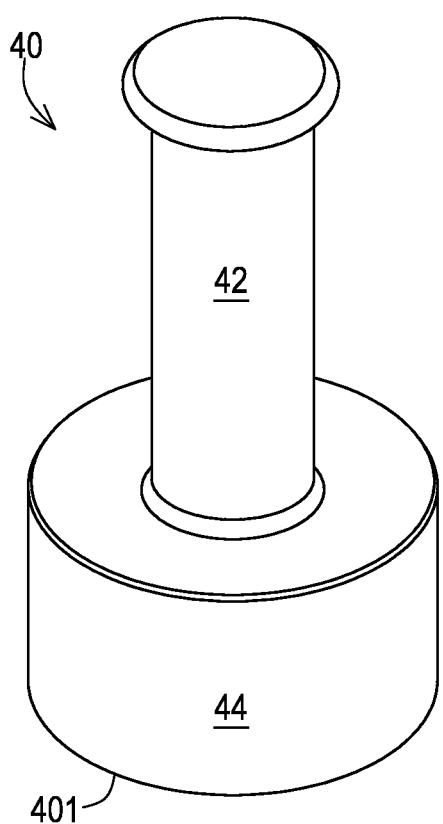
FIGS. 11A-11C depict three exemplary external magnets suitable for use with the feeding tube apparatus of the present invention.
Figure 11B:
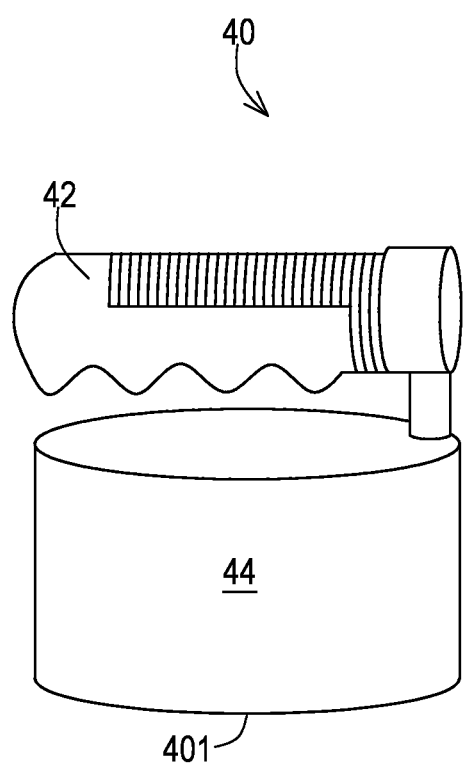
Figure 11C:
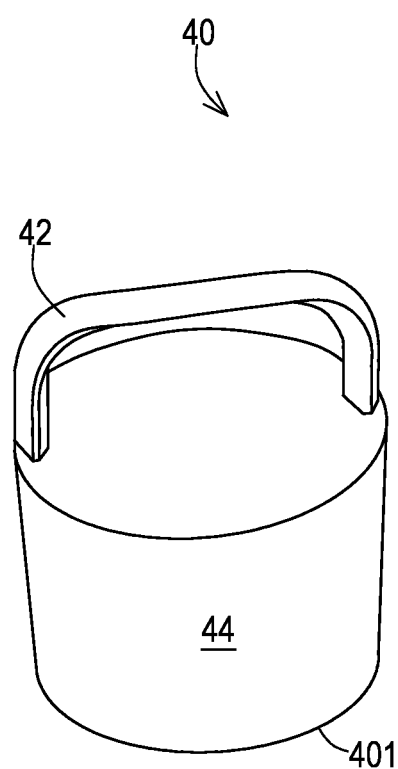

External magnets 40 can have any suitable shape or size that allows manipulation by the healthcare provider. FIGS. 11A-11C depict three exemplary external magnets 40 suitable for use with feeding tube apparatus 10 of the present invention. Each external magnet 40 typically has a handle 42 attached to a base magnet 44. Handle 42 may be affixed perpendicularly to base magnet 44, as shown in FIG. 11A. Alternatively, handle 42 may be attached to base magnet 44 so that it is parallel with base magnet 44, as shown in FIGS. 11B and 11C.

Base magnet 44 may have a wide range of dimensions and shapes. In one embodiment, base magnet 44 contains a surface 401 distal to handle 42 which is flat. Surface 401 is designed to be placed in contact with a patient's body. In one embodiment, base magnet 44 is in the shape of a cylinder. In other embodiments (not shown), base magnet 44 may be in the shape of a disc.

Typical diameters for base magnet 44 range from about 1 inch to about 5 inches, preferably from about 3 inches to about 4 inches. Typical heights for external magnet 40 (i.e., both handle 42 and base magnet 44) range from about 3 inches to about 8 inches, preferably from about 3 inches to about 6 inches.

One preferred material for base magnet 44 is Nedoymium N50 grade, which can be used to form a small and lightweight magnet that provides the highest practical magnetic flux for its size and weight.

Kits of the present invention may further include one or more additional components that assist the medical practitioner in use of feeding tube apparatus 10. Suitable additional components include, but are not limited to, a syringe, preferably a 60 CC syringe; one or more towels; one or more cups; disposable gloves; Xylocaine gel (e.g. 2% Xylocaine gel); tape; gauze; disposable magnet covers; spring wire guide, and/or pH paper. Kits may further comprise a plunger or obturator that can clear clogs in catheter 20 to eliminate the need to remove catheter 20 and replace with another one. Kits may also comprise a spring wire guide that can be inserted into catheter 20 after removable stylet 30 is removed.

III. Methods of Using Feeding Tube Apparatus

The present invention is further directed to methods of using the disclosed feeding tube apparatus 10 comprising an inflatable balloon component 282. In one exemplary embodiment, the method of using the disclosed feeding tube apparatus 10 comprises a method for intubating a patient 480 (see, FIG. 12) so as to introduce one or more nutrients into the duodenum of the patient, wherein the method comprises: guiding catheter 20 of feeding tube apparatus 10 through the patient's stomach 380 until inflatable balloon component 282 of catheter 20 passes through the pyloric sphincter 450; and inflating inflatable balloon component 282 of catheter 20 so as to allow natural peristalsis of the patient 480 to further advance feeding tube apparatus 10 comprising an inflated balloon component into the patient's duodenum 460.

The distal tip 25 of catheter 20 is introduced into the naris 350 of the patient's nose and advanced by the continued application of a compressive force to catheter 20 forcing distal tip 25 to the back portion of the patient's head and into the esophagus. As is common, the passageway of the esophagus affords ample guidance to distal tip 25 whereupon it enters the body portion of the stomach 380.

Figure 12:
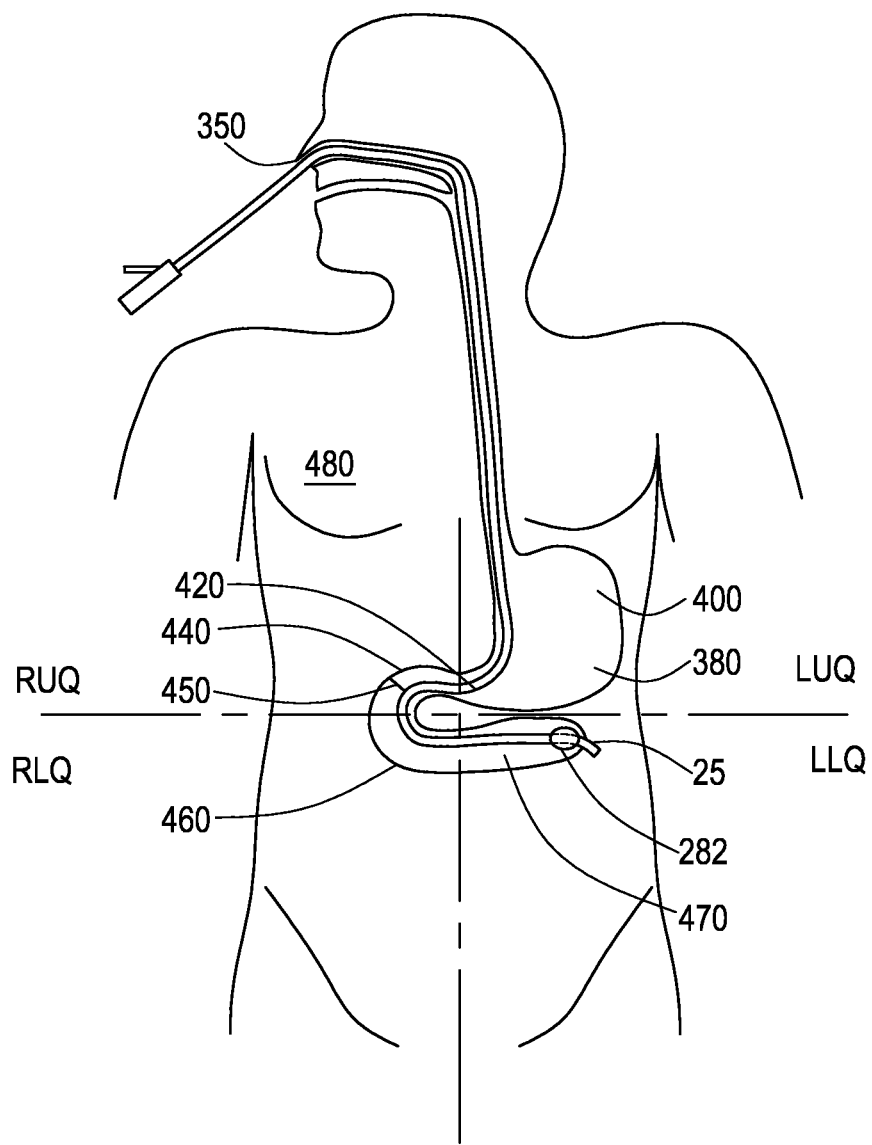
FIG. 12 depicts an illustration showing the path of an exemplary feeding tube apparatus of the present invention within anatomical quadrants during passage through the stomach to the distal duodenum of the small intestine.

FIG. 12 is an illustration showing the path of catheter 20 within anatomical quadrants of the small intestine abdomen. Catheter 20 passes through the stomach 380 to the distal duodenum 470 to allow for feeding to occur in distal duodenum 470, and thereby prevent aspiration of fluids to stomach 380, and subsequently into the esophagus and lung in supine patients.

After catheter 20 is placed in the desired location, removable stylet 30 is removed. Catheter 20 can remain in place when the patient 480 undergoes diagnostic tests, such as MRI imaging, since the magnet 32 or magnet stack 33 is removed from catheter 20 when removable stylet 10 is removed.

Stomach 380 has a generally J-shaped configuration extending with generally its largest transverse anatomical size at about the cardiac orifice, the entrance site to stomach 380, and then proceeding in the direction at which stomach 380 functions to advance bolus, the transverse dimension of stomach 380 narrows, and at an angular notch 420 which is generally at the border between the left upper quadrant (LUQ) and the right upper quadrant (RUQ). From annular notch 420, there commences a smaller transverse dimension at the pyloric part 440 typically residing in the right upper quadrant together with pyloric sphincter 450. Pyloric sphincter 450 is a muscular controlled closure, which will dilate as when a bolus comes into contact with the sphincter. Beyond the sphincter, a bolus passes into the duodenum portion 460 that extends to the right lower quadrant (RLQ), and then extends in a general horizontal direction into the left lower quadrant (LLQ) where the distal duodenum 470 of the small intestine is located.

Other Embodiments

Feeding Tube Apparatus:

1. A feeding tube apparatus 10 comprising a catheter 20 suitable for use with a removable stylet 30, said catheter 20 comprising a catheter proximal end 22, a catheter distal end 24 opposite said catheter proximal end 22, a catheter channel 26 extending along a length $L_c$ of said catheter 20 from said catheter proximal end 22 towards said catheter distal end 24, and an inflatable balloon component 282 positioned along said catheter 20 proximate said catheter distal end 24.

2. The feeding tube apparatus 10 of embodiment 1, wherein said catheter channel 26 extends less than a complete length of said catheter 20.

3. The feeding tube apparatus 10 of embodiment 1 or 2, wherein said catheter channel 26 extends a complete length of said catheter 20.

4. The feeding tube apparatus 10 of embodiment 1 or 3, wherein said catheter distal end 24 comprises a catheter distal end tip 25, and said catheter distal end tip 25 is open (e.g., as shown in FIGS. 2A-2B). Note, in other embodiments, the catheter distal end tip 25 may be closed (e.g., as shown in FIGS. 1A-1B).

5. The feeding tube apparatus 10 of any one of embodiments 1 to 4, wherein said inflatable balloon component 282 is positioned a distance $d_b$ from a catheter distal end tip 25 of said catheter 20.

6. The feeding tube apparatus 10 of any one of embodiments 1 to 5, wherein said inflatable balloon component 282 is positioned a distance $d_b$ of from about 1.0 centimeter (cm) to about 10.0 cm from a catheter distal end tip 25 of said catheter 20 (or any other distance $d_b$ from the catheter distal end tip 25 of said catheter 20 from greater than about 0.5 cm to about 10 cm, in increments of 0.1 cm, or any range of distances $d_b$ between about 1.0 cm and about 10 cm, in increments of 0.1 cm, e.g., from about 1.0 to about 2.0 cm, with 1.5 cm being a preferred distance $d_b$ in some embodiments).

7. The feeding tube apparatus 10 of any one of embodiments 1 to 6, wherein said inflatable balloon component 282 extends along an outer surface 27 of said catheter 20. Inflatable balloon component 282 may be attached to outer surface 27 of catheter 20 via any known attaching member (not shown). Suitable attaching members include, but are not limited to, an adhesive, and a mechanical bond (e.g., an ultrasonic welding bond).

8. The feeding tube apparatus 10 of any one of embodiments 1 to 7, wherein said inflatable balloon component 282 is sized so as to contain up to 20 milliliters (ml) of inflating fluid 91 (see, FIG. 4) (or any amount up to 20 ml, or any range between greater than 0 ml to about 20 ml, in increments of 0.1 ml, with about 3.0 ml being preferred for adult patients, and about 1.0 ml being preferred for smaller, pediatric patient).

9. The feeding tube apparatus 10 of any one of embodiments 1 to 8, wherein said inflatable balloon component 282 is sized so as to contain from about 1.0 ml to about 5.0 ml of inflating fluid 91.

10. The feeding tube apparatus 10 of any one of embodiments 1 to 9, wherein said inflatable balloon component 282 contains from about 1.0 ml to about 5.0 ml of inflating fluid 91.

11. The feeding tube apparatus 10 of embodiment 10, wherein said inflating fluid 91 comprises water. It should be noted that, in other embodiments, the inflating fluid 91 may comprise another type of fluid, such as air.

12. The feeding tube apparatus 10 of any one of embodiments 1 to 11, wherein said catheter 20 further comprises one or more inflating holes 29 with each inflating hole 29 having an inflating hole outlet 291 along an outer surface 27 of said catheter 20 positioned underneath said inflatable balloon component 282. Typically, the catheters 20 of the present invention comprise a single inflating hole 29 or up to about four inflating holes 29.

13. The feeding tube apparatus 10 of any one of embodiments 1 to 11, wherein said catheter 20 further comprises one or more inflating channels 29' extending along a length $L_c$ of said catheter 20 and within a sidewall 201 of said catheter 20, each of said one or more inflating channels 29' comprising an inflating channel inlet opening 292 proximate said catheter proximal end 22 and an inflating channel outlet opening 291 along an outer surface 27 of said catheter 20 positioned underneath said inflatable balloon component 282. Typically, the catheters 20 of the present invention comprise a single inflating channel 29' or up to about four inflating channels 29'.

14. The feeding tube apparatus 10 of any one of embodiments 1 to 13, wherein said catheter 20 further comprises one or more inflation tubes 202 attached to said catheter 20 along an outer surface 27 of said catheter 20 proximate said catheter proximal end 22. Typically, the one or more inflation tubes 202 are attached to the catheter 20 along an outer surface 27 of said catheter 20 as shown in FIG. 5. Each inflation tube 202 may be attached to catheter 20 along outer surface 27 via any known attaching member (not shown). Suitable attaching members include, but are not limited to, an adhesive, and a mechanical bond (e.g., an ultrasonic welding bond). Typically, the catheters 20 of the present invention comprise a single inflation tube 202, even though the catheters 20 of the present invention may comprise more than one inflation tube 202.

15. The feeding tube apparatus 10 of embodiment 14, further comprising one or more pilot balloons 203 positioned along and in fluid communication with said single inflation tube 202, pilot balloon 203 being positioned so as to indicate whether said inflatable balloon component 282 is inflated or deflated.

16. The feeding tube apparatus 10 of embodiment 14 or 15, further comprising one or more inflating devices 288 operatively adapted to provide inflating fluid 91 through said one or more inflation tubes 202 and into said inflatable balloon component 282. Typically, the catheters 20 of the present invention comprise a single inflating device 288, even though the catheters 20 of the present invention may comprise more than one inflating device 288.

17. The feeding tube apparatus 10 of embodiment 16, wherein said one or more inflating devices 288 comprise a syringe 288 (see, FIG. 13). (The syringe 288 may be connected to inflation tube 202 at port/valve 205 as shown in FIGS. 5 and 13 so as to input water or another fluid into inflation tube 202.)

18. The feeding tube apparatus 10 of any one of embodiments 1 to 17, wherein said catheter 20 further comprises one or more valves 205 that temporarily prevent inflating fluid 91 from exiting said inflatable balloon component 282 once inflated. Typically, the catheters 20 of the present invention comprise a single valve 205 for the catheter 20 or a single valve 205 for each inflation tube 202. Each valve 205 may comprise a one-way valve that allow fluid flow in a single direction (i.e., fluid flow into inflatable balloon component 282) or a two-way valve that allow fluid flow in two directions (i.e., fluid flow into and out of inflatable balloon component 282). Although valve 205 is shown in FIG. 5 at an end 206 of inflation tube 202, it should be understood that one or more valves 205 may be positioned at any location along the length of inflation tube 202.

19. The feeding tube apparatus 10 of any one of embodiments 14 to 18, wherein said catheter 20 further comprises one or more valves 205 that temporarily prevent inflating fluid 91 from exiting said inflatable balloon component 282 once inflated, said one or more valves 205 being positioned along said one or more inflation tubes 202. As discussed above, in some embodiments, the catheters 20 of the present invention comprise a single valve 205 along each inflation tube 202.

20. The feeding tube apparatus 10 of any one of embodiments 1 to 19, wherein said catheter 20 further comprises one or more visual markers 208 extending along an outer surface 27 of said catheter 20, each of said one or more visual markers 208 providing a visual indication of a catheter length extending from a catheter distal end tip 25 to a given visual marker 208. In other words, the visual markers provide a visual reference that indicates a position (i.e., distance) of the catheter distal end tip 25 of the feeding tube 10 within a patient.

21. The feeding tube apparatus 10 of any one of embodiments 1 to 20, wherein said catheter 20 further comprises two or more sets of one or more visual markers 208 (e.g., sets 208a, 208b and 208c shown in FIG. 1A) extending along an outer surface 27 of said catheter 20, each of said one or more visual markers 208 providing a visual indication of a catheter length extending from a catheter distal end tip 25 to a given visual marker.

22. The feeding tube apparatus 10 of embodiment 21, wherein said two or more sets of one or more visual markers 208 comprise (i) a single visual marker 208a at a distance of about 50 cm from a catheter distal end tip 25, (ii) two adjacent visual markers 208b at a distance of about 80 cm from said catheter distal end tip 25, and (iii) three adjacent visual markers 208c at a distance of about 110 cm from said catheter distal end tip 25. For example, the 50 cm mark 208a may correspond to a lower end of the patient's esophagus, the 80 cm mark 208b may correspond to the first part of the patient's duodenum, and the 110 cm mark 208c may correspond to the catheter distal tip 25 being within the 4$^{th}$ part of the patient's duodenum in an adult size patient.

23. The feeding tube apparatus 10 of any one of embodiments 1 to 22, wherein said catheter 20 further comprises one or more side holes 28, wherein each side hole 28 (1) extends from an inner surface 261 of said catheter 20 along said catheter channel 26 to an outer surface 27 of said catheter 20, and (2) is positioned (i) between said inflatable balloon component 282 and a catheter distal end tip 25, (ii) between said inflatable balloon component 282 and said catheter proximal end 22, or (iii) both (i) and (ii). Typically, the catheters 20 of the present invention comprise two or more side holes 28, more typically, from about 1 to about 4 side holes 28. See, for example, side holes 28 shown in FIGS. 1A-2B.

24. The feeding tube apparatus 10 of embodiment 23, wherein at least one of said side holes 28 is positioned between said inflatable balloon component 282 and a catheter distal end tip 25.

25. The feeding tube apparatus 20 of any one of embodiments 1 to 24, wherein said catheter 20 further comprises a feeding tube hub 80 positioned at said catheter proximal end 22, said feeding tube hub 80 comprising one or more hub ports 82 to allow for aspiration or delivery of medications via said catheter 20.

26. The feeding tube apparatus 10 of any one of embodiments 1 to 25, wherein said catheter 20 further comprises a feeding tube hub 80 positioned at said catheter proximal end 22, said feeding tube hub 80 comprising two or more hub ports 82 to allow for aspiration or delivery of medications via said catheter 20. Typically, the catheters 20 of the present invention comprise two to three hub ports 82.

27. The feeding tube apparatus 10 of any one of embodiments 1 to 26, wherein a wall 201 of said catheter 20 (see, FIG. 5) extending along a length $L_c$ of said catheter 20 comprises an MRI compatible reinforcing material 222. In some embodiments, the MRI compatible reinforcing material 222 comprising a coil reinforcing material 222 extending along a length $L_c$ of said catheter 20 and within or along an inner portion of said wall 201 with individual coils of said coil reinforcing material 222 extending substantially perpendicular to length $L_c$ of catheter 20 (see, FIGS. 3-5).

28. The feeding tube apparatus 10 of any one of embodiments 1 to 27, wherein a wall 201 of said catheter 20 extending along a length $L_c$ of said catheter 20 comprises medical grade radio-opaque material. Suitable medical grade radio-opaque materials include, but are not limited to, polyvinyl chloride (PVC), and polyurethane loaded with from about 20 wt % to about 40 wt % barium sulfate or bismuth subsalicylate.

29. The feeding tube apparatus 10 of any one of embodiments 1 to 28, further comprising a removable stylet 30, said removable stylet 30 comprising a stylet proximal end 31 and a stylet distal end 34 opposite said stylet proximal end 31, said stylet distal end 34 being sized so as to be insertable within (i) a catheter opening 23 at said catheter proximal end 22, and (ii) said catheter channel 26.

30. The feeding tube apparatus 10 of embodiment 29, wherein said removable stylet 30 comprises a stylet hub 90 at said stylet proximal end 31.

31. The feeding tube apparatus 10 of embodiment 29 or 30, wherein said removable stylet 30 further comprises one or more magnetic materials 32 proximate said stylet distal end 34. Suitable magnet configurations of the one or more magnetic materials 32 are shown in FIG. 6. Other suitable magnet configurations of the one or more magnetic materials 32 are disclosed in U.S. Pat. No. 6,126,647, the subject matter of which is hereby incorporated herein in its entirety.

32. The feeding tube apparatus 10 of any one of embodiments 29 to 31, wherein said removable stylet 30 further comprises a reed switch assembly 60, said reed switch assembly 60 being operatively adapted to activate when a magnetic force between (i) one or more magnetic materials 32 positioned proximate said stylet distal end 34 of said removable stylet 30 and (ii) an external magnet 40 (see, FIGS. 11A-11C) is sufficiently strong to move said catheter 20 (and/or said removable stylet 30) along an intestinal tract using the external magnet 40. A suitable reed switch assembly 60 is shown in FIG. 6. Other suitable reed switch assemblies 60 are disclosed in U.S. Pat. No. 6,126,647, the subject matter of which is hereby incorporated herein in its entirety.

33. The feeding tube apparatus 10 of any one of embodiments 29 to 32, wherein said removable stylet 30 further comprises a signal generator 50 connected to said stylet proximal end 31, said signal generator 50 being operatively adapted to generate and emit a signal selected from the group consisting of light, sound, vibration, and digital readout in response to detecting a threshold amount of a magnetic force between (i) one or more magnetic materials 32 positioned proximate said stylet distal end 34 of said removable stylet 30 and (ii) an external magnet 40. A suitable signal generator 50 is shown in FIGS. 1A and 7. Other suitable signal generators are disclosed in U.S. Pat. No. 6,126,647, the subject matter of which is hereby incorporated herein in its entirety.

34. The feeding tube apparatus 10 of embodiment 33, wherein said signal generator 50 comprises an indicator 52 comprising a light emitting diode (LED).

35. The feeding tube apparatus 10 of any one of embodiments 29 to 34, wherein said removable stylet 30 further comprises a spring wire guide 48, wherein said spring wire guide 48 extends from a distal tip 35 of said removable stylet 30. Suitable spring wire guides 48 are shown in FIGS. 10A-10C. Other suitable spring wire guides 48 are disclosed in U.S. Pat. No. 6,126,647, the subject matter of which is hereby incorporated herein in its entirety.

36. The feeding tube apparatus 10 of any one of embodiments 32 to 35, wherein said removable stylet 30 further comprises a spring wire guide 48, wherein said spring wire guide 48 terminates proximate said reed switch 60.
37. The feeding tube apparatus 10 of any one of embodiments 29 to 36, wherein said removable stylet 30 further comprises a pigtail-shaped spring wire guide 48, wherein said pigtail-shaped spring wire guide 48 extends from a distal tip 35 of said removable stylet 30.
38. The feeding tube apparatus 10 of any one of embodiments 29 to 37, wherein said removable stylet 30 is formed from a dual durometer material. Suitable dual durometer materials include, but are not limited to, nylon, polyether ether ketone (PEEK), ESTANE® polymers (The Lubrizol Corporation), and PEBAX® polymers (Arkema).
39. The feeding tube apparatus 10 of any one of embodiments 29 to 38, wherein said removable stylet 30 or catheter 20 outer wall further comprises a pH sensor (not shown) thereon.
40. The feeding tube apparatus 10 of any one of embodiments 29 to 39, wherein said removable stylet 30 has an overall length $L_s$ (see, FIG. 7) equal to or greater than an overall length of said catheter 20.
41. The feeding tube apparatus 10 of any one of embodiments 29 to 40, wherein said removable stylet 30 has an overall length $L_s$ greater than an overall length $L_c$ of said catheter 20.
42. The feeding tube apparatus 10 of any one of embodiments 29 to 41, wherein said removable stylet 30 has an overall length $L_s$ that is greater than an overall length of said catheter 20 by about 40 cm. Typically, the catheter 20 has an overall length $L_c$ ranging from about 100 to about 150 cm, while the removable stylet 30 has an overall length $L_s$ ranging from about 100 to about 200 cm.

Kits Comprising a Feeding Tube Apparatus:

43. A kit comprising the feeding tube apparatus 10 of any one of embodiments 1 to 42, and an external magnet 40. See, for example, exemplary external magnets 40 in FIGS. 11A-11C.
44. The kit of embodiment 43, wherein the external magnet 40 comprises a handle 42 and a base magnet 44.
45. The kit of embodiment 43 or 44, wherein the external magnet 40 is a permanent magnet 40.
46. The kit of any one of embodiments 43 to 45, further comprising a spring wire guide 48, a plunger (not shown), a syringe, pH paper, or any combination thereof.

Methods of Using Feeding Devices:

47. A method for intubating a patient 480 (see, FIG. 12) so as to introduce one or more nutrients into the duodenum 460 of the patient 480, said method comprising: guiding the catheter 20 of the feeding tube apparatus 10 of any one of embodiments 1 to 42 through the patient's stomach 380 until the inflatable balloon component 282 of the catheter 20 passes through the pyloric sphincter 450; and inflating the inflatable balloon component 282 of the catheter 20 so as to allow natural peristalsis of the patient 480 to further advance the feeding tube apparatus 10 comprising an inflated balloon component into the patient's duodenum 460/470.
48. The method of embodiment 47, wherein said inflating step comprises inflating the inflatable balloon component 282 with water 91.
49. The method of embodiment 48, wherein said inflating step further comprises closing a valve 205 to prevent the water 91 from exiting the inflatable balloon component 282.
50. The method of any one of embodiments 47 to 49, wherein said guiding step comprises: introducing a distal tip 25 of the catheter 20 into the patient's nose 350; and pushing the catheter 20 through the patient's esophagus and into the patient's stomach 380.
51. The method of embodiment 50, wherein said guiding step further comprises: advancing the removable stylet 30 beyond the distal tip 25 of the catheter 20 into the patient's duodenum 470; and pushing the catheter 20 over the removable stylet 30 so as to advance the catheter 20.
52. The method of embodiment 50 or 51, wherein said guiding step further comprises: arranging an external magnet 40 on the patient's abdomen; and guiding the catheter 20 through the patient's stomach 380 using a magnetic field between the external magnet 40 and one or more magnetic materials 32 in the distal end 34 of the removable stylet 30 until the inflatable balloon component 282 of the catheter 20 passes through the pyloric sphincter 450.
53. The method of any one of embodiments 47 to 52, wherein said method further comprises: removing the removable stylet 30 from the catheter 20.
54. The method of any one of embodiments 47 to 53, wherein said method further comprises: conducting an x-ray procedure so as to verify a position of the catheter 20 within the patient 480.
55. The method of any one of embodiments 47 to 55, wherein said method further comprises: delivering one or more nutrients to the patient 480 through one or more openings 28 within the catheter 20.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of Feeding Tube Apparatus

Exemplary feeding tube apparatus as shown in FIGS. 1A-13 were prepared using conventional steps (e.g., one or more thermoforming steps, and one or more connection/assembly steps).

It should be understood that although the above-described feeding tube apparatus, kits and methods are described as "comprising" one or more components or steps, the above-described feeding tube apparatus, kits and methods may "comprise," "consists of," or "consist essentially of" any of the above-described components, features or steps of the feeding tube apparatus, kits and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a feeding tube apparatus, kit and/or method that "comprises" a list of elements (e.g., components, features or steps) is not necessarily limited to only those elements (or components or steps), but may include other elements (or components or steps) not expressly listed or inherent to the feeding tube apparatus, kit and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a feeding tube apparatus, kit and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described feeding tube apparatus, kits and/or methods may comprise, consist essentially of, or consist of any of the herein-described components and features, as shown in the figures with or without any feature(s) not shown in the figures. In other words, in some embodiments, the feeding tube apparatus, kits and/or methods of the present invention do not have any additional features other than those shown in the figures, and such additional features, not shown in the figures, are specifically excluded from the feeding tube apparatus, kits and/or methods. In other embodiments, the feeding tube apparatus, kits and/or methods of the present invention do have one or more additional features that are not shown in the figures.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A feeding tube apparatus sized for insertion through a patient's naris and having a length that extends from outside the patient's nose to the patient's small intestines, said feeding tube apparatus comprising:
    a catheter comprising:
        a catheter tube having an outer diameter of up to about 4.0 millimeter (mm),
        a catheter proximal end,
        a catheter distal end opposite said catheter proximal end,
        a single catheter channel extending along a length of said catheter tube from said catheter proximal end to said catheter distal end,
        an inflatable balloon component positioned along an outer surface of said catheter tube proximate said catheter distal end, said inflatable balloon component being sized so as to contain from about 1.0 milliliter (ml) to about 3.0 ml of inflating fluid,
        a single inflating channel extending along the length of said catheter tube and within a sidewall of said catheter tube, said single inflating channel comprising an inflating channel inlet opening proximate said catheter proximal end and an inflating channel outlet opening along an outer surface of said catheter tube positioned underneath said inflatable balloon component,
        a coil reinforcing material extending along and forming an inner surface of said sidewall with individual coils of said coil reinforcing material extending substantially perpendicular to said length of said catheter tube,
        one or more side holes, wherein each side hole (1) extends from said inner surface of said catheter tube sidewall along said single catheter channel to an outer surface of said catheter tube, and (2) is positioned between said inflatable balloon component and a catheter distal end tip,
        a single inflation tube attached to said catheter tube along an outer surface proximate said catheter proximal end,
        a single pilot balloon positioned along and in fluid communication with said single inflation tube, said pilot balloon being positioned so as to indicate whether said inflatable balloon component is inflated or deflated, and
        a single valve that temporarily prevents inflating fluid from exiting said inflatable balloon component once inflated; and
    a removable stylet comprising:
        a stylet proximal end, and
        a stylet distal end opposite said stylet proximal end, said stylet distal end being sized so as to be insertable within (i) a catheter opening at said catheter proximal end, and (ii) said single catheter channel.

2. The feeding tube apparatus of claim 1, further comprising one or more inflating devices operatively adapted to provide inflating fluid through said one or more inflation tubes and into said inflatable balloon component.

3. The feeding tube apparatus of claim 1, wherein said catheter further comprises a feeding tube hub positioned at said catheter proximal end, said feeding tube hub comprising one or more hub ports to allow for aspiration or delivery of medications via said catheter.

4. The feeding tube apparatus of claim 1, wherein said coil reinforcing material comprises an MRI compatible reinforcing material.

5. The feeding tube apparatus of claim 1, wherein said removable stylet further comprises one or more magnetic materials proximate said stylet distal end.

6. A kit comprising the feeding tube apparatus of claim 1, and a syringe, pH paper, tape, or any combination thereof.

7. A method for intubating a patient so as to introduce one or more nutrients into the duodenum of the patient, said method comprising:
    guiding the catheter of the feeding tube apparatus of claim 1 through the naris of the patient's nose and into the patient's intestinal tract; and inflating the inflatable balloon component of the catheter so as to allow natural peristalsis of the patient to further advance the feeding tube apparatus comprising an inflated balloon component into the patient's duodenum.

8. The method of claim 7, wherein said method further comprises:
delivering one or more nutrients to the patient through one or more openings within the catheter tube.

9. The feeding tube apparatus of claim 1, wherein said catheter tube has an overall length of from about 100 cm up to about 150 cm.

10. A feeding tube apparatus sized for insertion through a patient's naris and having a length that extends from outside the patient's nose to the patient's small intestines, said feeding tube apparatus comprising:
a catheter comprising:
a catheter tube having an outer diameter of up to about 4.0 mm and an overall length of up to about 150 cm,
a catheter proximal end,
a catheter distal end opposite said catheter proximal end,
a single catheter channel extending along a length of said catheter tube from said catheter proximal end to said catheter distal end,
an inflatable balloon component positioned along an outer surface of said catheter tube proximate said catheter distal end,
a single inflating channel extending along the length of said catheter tube and within a sidewall of said catheter tube, said single inflating channel comprising an inflating channel inlet opening proximate said catheter proximal end and an inflating channel outlet opening along an outer surface of said catheter tube positioned underneath said inflatable balloon component,
a single inflation tube attached to said catheter tube along an outer surface proximate said catheter proximal end,
a single pilot balloon positioned along and in fluid communication with said single inflation tube, said pilot balloon being positioned so as to indicate whether said inflatable balloon component is inflated or deflated, and
one or more valves that temporarily prevent inflating fluid from exiting said inflatable balloon component once inflated;
wherein a wall of said catheter tube extending along a length of said catheter tube comprises a metal coil reinforcing material extending along and forming an inner surface of said wall with individual coils of said metal coil reinforcing material extending substantially perpendicular to said length of said catheter tube; and
a removable stylet comprising:
a stylet proximal end, and
a stylet distal end opposite said stylet proximal end, said stylet distal end being sized so as to be insertable within (i) a catheter opening at said catheter proximal end, and (ii) said single catheter channel, and when said removable stylet is fully inserted within said catheter tube, said stylet distal end of said removable stylet is positioned within said single catheter channel and at a distance from a tip of said catheter distal end.

11. The feeding tube apparatus of claim 10, wherein said catheter tube further comprises one or more side holes, wherein each side hole (1) extends from said inner surface of said catheter sidewall along said single catheter channel to an outer surface of said catheter tube, and (2) is positioned between said inflatable balloon component and a catheter distal end tip.

12. The feeding tube apparatus of claim 10, wherein said inflatable balloon component is sized so as to contain from about 1.0 milliliter (ml) to about 3.0 ml of inflating fluid.

13. A method for intubating a patient so as to introduce one or more nutrients into the duodenum of the patient, said method comprising:
guiding the catheter of the feeding tube apparatus of claim 10 through the naris of the patient's nose and into the patient's intestinal tract; and
inflating the inflatable balloon component of the catheter so as to allow natural peristalsis of the patient to further advance the feeding tube apparatus comprising an inflated balloon component into the patient's duodenum.

14. A kit comprising the feeding tube apparatus of claim 10, and a syringe, pH paper, tape, or any combination thereof.

15. A feeding tube apparatus sized for insertion through a patient's naris and having a length that extends from outside the patient's nose to the patient's small intestines, said feeding tube apparatus comprising:
a catheter comprising:
a catheter tube having an outer diameter of up to about 4.0 mm,
a catheter proximal end,
a catheter distal end opposite said catheter proximal end,
a single catheter channel extending along a length of said catheter tube from said catheter proximal end to said catheter distal end,
an inflatable balloon component positioned along an outer surface of said catheter tube proximate said catheter distal end, said inflatable balloon component being sized so as to contain from about 1.0 milliliter (ml) to about 3.0 ml of inflating fluid,
a single inflating channel extending along the length of said catheter tube and within a sidewall of said catheter tube, said single inflating channel comprising an inflating channel inlet opening proximate said catheter proximal end and an inflating channel outlet opening along an outer surface of said catheter tube positioned underneath said inflatable balloon component,
a coil reinforcing material extending along and forming an inner surface of said sidewall with individual coils of said coil reinforcing material extending substantially perpendicular to said length of said catheter tube,
one or more side holes, wherein each side hole (1) extends from said inner surface of said catheter sidewall along said single catheter channel to an outer surface of said catheter tube, and (2) is positioned between said inflatable balloon component and a catheter distal end tip,
a single inflation tube attached to said catheter tube along an outer surface proximate said catheter proximal end,
a single pilot balloon positioned along and in fluid communication with said single inflation tube, said pilot balloon being positioned so as to indicate whether said inflatable balloon component is inflated or deflated, and one or more valves that temporarily prevent inflating fluid from exiting said inflatable balloon component once inflated; and a removable stylet comprising:
- a stylet proximal end, and
- a stylet distal end opposite said stylet proximal end, said stylet distal end being sized so as to be insertable within (i) a catheter opening at said catheter proximal end, and (ii) said single catheter channel.

16. The feeding tube apparatus of claim 15, wherein said coil reinforcing material comprises an MM compatible reinforcing material.

17. The feeding tube apparatus of claim 15, wherein said catheter tube has an overall length of from about 100 cm up to about 150 cm.

18. The feeding tube apparatus of claim 15, wherein when said removable stylet is fully inserted within said catheter tube, said stylet distal end of said removable stylet is positioned within said single catheter channel and at a distance from a tip of said catheter distal end.

19. A kit comprising the feeding tube apparatus of claim 15, and a syringe, pH paper, tape, or any combination thereof.

20. A method for intubating a patient so as to introduce one or more nutrients into the duodenum of the patient, said method comprising:
- guiding the catheter of the feeding tube apparatus of claim 15 through the naris of the patient's nose and into the patient's intestinal tract; and
- inflating the inflatable balloon component of the catheter so as to allow natural peristalsis of the patient to further advance the feeding tube apparatus comprising an inflated balloon component into the patient's duodenum.

* * * * *

UNITED STATES PATENT AND TRADEMARK OFFICE
CERTIFICATE OF CORRECTION

PATENT NO. : 9,713,578 B2
APPLICATION NO. : 14/108422
DATED : July 25, 2017
INVENTOR(S) : Sabry Gabriel It is certified that error appears in the above-identified patent and that said Letters Patent is hereby corrected as shown below:

In the Specification

Please insert in Column 1, Line 13, after Cross-Reference to Related Applications:
--The Statement of Governmental Interest
This invention was made with Government support under grant number W81XWH-09-2-0097, awarded by the U.S. Army Medical Research and Materiel Command (ARMY/MRMC). The U.S. Government has certain rights in this invention.--

Signed and Sealed this
Second Day of March, 2021

Drew Hirshfeld
*Performing the Functions and Duties of the
Under Secretary of Commerce for Intellectual Property and
Director of the United States Patent and Trademark Office*